(12) United States Patent
Trinklein et al.

(10) Patent No.: US 11,421,027 B2
(45) Date of Patent: *Aug. 23, 2022

(54) CD3 BINDING ANTIBODIES

(71) Applicant: TeneoOne, Inc., Newark, CA (US)

(72) Inventors: Nathan Trinklein, Newark, CA (US); Wim van Schooten, Newark, CA (US); Shelley Force Aldred, Newark, CA (US); Katherine Harris, Newark, CA (US); Duy Pham, Newark, CA (US)

(73) Assignee: TeneoOne, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/492,444

(22) Filed: Oct. 1, 2021

(65) Prior Publication Data

US 2022/0025047 A1 Jan. 27, 2022

Related U.S. Application Data

(62) Division of application No. 16/332,665, filed as application No. PCT/US2017/038377 on Jun. 20, 2017.

(60) Provisional application No. 62/491,908, filed on Apr. 28, 2017, provisional application No. 62/394,360, filed on Sep. 14, 2016.

(51) Int. Cl.
C07K 16/28 (2006.01)

(52) U.S. Cl.
CPC ...... *C07K 16/2809* (2013.01); *C07K 16/2878* (2013.01); *C07K 2317/31* (2013.01); *C07K 2317/52* (2013.01); *C07K 2317/565* (2013.01); *C07K 2317/567* (2013.01); *C07K 2317/622* (2013.01); *C07K 2317/71* (2013.01); *C07K 2317/732* (2013.01); *C07K 2317/734* (2013.01); *C07K 2317/92* (2013.01)

(58) Field of Classification Search
CPC .......... C07K 16/2809; C07K 2317/565; C07K 2317/569
USPC .......................................... 424/133.1, 136.1
See application file for complete search history.

(56) References Cited

U.S. PATENT DOCUMENTS

| | | | |
|---|---|---|---|
| 4,816,567 A | 3/1989 | Cabilly et al. |
| 5,500,362 A | 3/1996 | Robinson et al. |
| 5,585,097 A | 12/1996 | Bolt et al. |
| 5,821,337 A | 10/1998 | Carter et al. |
| 5,929,212 A | 7/1999 | Jolliffe et al. |
| 5,968,509 A | 10/1999 | Gorman et al. |
| 6,706,265 B1 | 3/2004 | Bolt et al. |
| 6,750,325 B1 | 6/2004 | Jolliffe et al. |
| 7,262,276 B2 | 8/2007 | Huang et al. |
| 7,381,803 B1 | 6/2008 | Weiner et al. |
| 7,541,513 B2 | 6/2009 | Bruggeman et al. |
| 7,635,472 B2 | 12/2009 | Kufer et al. |
| 7,728,114 B2 | 6/2010 | MacH et al. |
| 7,862,813 B2 | 1/2011 | Bjork et al. |
| 8,236,308 B2 | 8/2012 | Kischel et al. |
| 8,367,888 B2 | 2/2013 | Bruggemann et al. |
| 8,883,150 B2 | 11/2014 | Craig et al. |
| 9,034,324 B2 | 5/2015 | Kalled et al. |
| 9,365,655 B2 | 6/2016 | Craig et al. |
| 2004/0229310 A1 | 11/2004 | Simmons |
| 2005/0048572 A1 | 3/2005 | Reilly et al. |
| 2007/0065437 A1 | 3/2007 | Elson et al. |
| 2007/0071675 A1 | 3/2007 | Wu et al. |
| 2009/0098134 A1 | 4/2009 | Buelow |
| 2010/0122358 A1 | 5/2010 | Bruggemann et al. |
| 2013/0156769 A1 | 6/2013 | Kufer et al. |
| 2013/0273055 A1 | 10/2013 | Borges et al. |
| 2013/0273066 A1 | 10/2013 | Borges et al. |
| 2015/0118251 A1 | 4/2015 | Deslandes et al. |
| 2015/0266966 A1 | 9/2015 | Smith et al. |
| 2015/0368351 A1 | 12/2015 | Vu et al. |
| 2015/0376287 A1 | 12/2015 | Vu et al. |
| 2016/0046724 A1 | 2/2016 | Brogdon et al. |
| 2016/0166689 A1 | 6/2016 | Adler et al. |
| 2016/0194399 A1 | 7/2016 | Irving et al. |
| 2016/0355591 A1 | 12/2016 | Goldenberg et al. |
| 2019/0225671 A1 | 7/2019 | van Schooten et al. |
| 2019/0263904 A1* | 8/2019 | Trinklein ............... A61P 35/02 |
| 2020/0048348 A1* | 2/2020 | Trinklein ........... C07K 16/2827 |
| 2020/0085839 A1 | 3/2020 | Sidransky et al. |
| 2020/0157232 A1* | 5/2020 | Trinklein ........... C07K 16/2809 |
| 2020/0339685 A1* | 10/2020 | Schellenberger .. C07K 16/2809 |
| 2021/0047402 A1 | 2/2021 | Trinklein et al. |

(Continued)

FOREIGN PATENT DOCUMENTS

| | | |
|---|---|---|
| CN | 105384825 | 3/2016 |
| JP | 2012504403 | 2/2012 |

(Continued)

OTHER PUBLICATIONS

Buelow et al (Journal of Clinical Oncology, (Feb. 2018) vol. 36, No. 5, Supp. Supplement 1. Abstract No. 60. Meeting Info: 2018 ASCO-SITC Clinical Immuno-Oncology Symposium. San Francisco, CA, United States. Jan. 25, 2018-Jan. 27, 2018).*

Buelow et al (Blood, (Nov. 2019) vol. 134, Supp. Supplement 1. Abstract No. 1874. Meeting Info: 61st Annual Meeting of the American Society of Hematology, ASH 2019. Orlando, FL, United States. Dec. 7, 2019-Dec. 10, 2019).*

(Continued)

*Primary Examiner* — Lynn A Bristol
(74) *Attorney, Agent, or Firm* — Jones Day

(57) ABSTRACT

The present invention relates to human CD3 antigen-binding polypeptides and their preparation and use in the treatment and/or diagnosis of various diseases, and also relates to bispecific antibody molecules capable of activating immune effector cells and their use in diagnosis and/or treatment of various diseases.

17 Claims, 12 Drawing Sheets

Specification includes a Sequence Listing.

(56) References Cited

U.S. PATENT DOCUMENTS

| | | | | |
|---|---|---|---|---|
| 2021/0340255 | A1* | 11/2021 | Harris | C07K 16/2878 |
| 2021/0355215 | A1* | 11/2021 | Jorgensen | C07K 16/2878 |

FOREIGN PATENT DOCUMENTS

| | | |
|---|---|---|
| JP | 2013528569 | 7/2013 |
| JP | 2015521032 | 7/2015 |
| RU | 2492186 | 9/2013 |
| RU | 2561457 C2 | 8/2015 |
| WO | 1996/027011 A1 | 9/1996 |
| WO | WO 1996/032478 | 10/1996 |
| WO | WO 1997/034631 | 9/1997 |
| WO | 1998/050431 A2 | 11/1998 |
| WO | 2001/024811 A1 | 4/2001 |
| WO | 2001/024812 A1 | 4/2001 |
| WO | WO 2001/077342 | 10/2001 |
| WO | 2002/066516 A2 | 8/2002 |
| WO | 2006/008548 A2 | 1/2006 |
| WO | WO 2007/066109 | 6/2007 |
| WO | WO 2007/117600 | 10/2007 |
| WO | WO 2009/132058 | 10/2009 |
| WO | 2010/109165 A2 | 9/2010 |
| WO | 2011/097603 A1 | 8/2011 |
| WO | WO 2012/066058 | 5/2012 |
| WO | WO 2012/122512 | 9/2012 |
| WO | WO 2012/122528 | 9/2012 |
| WO | WO 2012/143498 | 10/2012 |
| WO | WO 2012/163805 | 12/2012 |
| WO | WO 2013/072406 | 5/2013 |
| WO | WO 2013/072415 | 5/2013 |
| WO | 2014/022540 A1 | 2/2014 |
| WO | 2014/047231 A1 | 3/2014 |
| WO | 2014/068079 A1 | 5/2014 |
| WO | 2014/089335 A2 | 6/2014 |
| WO | 2014/093908 A2 | 6/2014 |
| WO | WO 2014/122144 | 8/2014 |
| WO | WO 2015/063339 | 5/2015 |
| WO | 2015/095412 A1 | 6/2015 |
| WO | 2015/121383 A1 | 8/2015 |
| WO | WO 2015/149077 | 10/2015 |
| WO | WO 2016/062990 | 4/2016 |
| WO | 2016/079081 A1 | 5/2016 |
| WO | 2016/079177 A1 | 5/2016 |
| WO | WO 2016/094304 | 6/2016 |
| WO | WO 2016/113555 | 7/2016 |
| WO | WO 2016/187546 | 11/2016 |
| WO | 2017/025038 A1 | 2/2017 |
| WO | 2017/031104 A1 | 2/2017 |
| WO | WO 2017/081211 | 5/2017 |
| WO | 2017/223111 A1 | 12/2017 |
| WO | 2018/052503 A1 | 3/2018 |
| WO | WO 2018/039180 | 3/2018 |
| WO | WO 2018/119215 | 6/2018 |
| WO | 2018/237006 A1 | 12/2018 |
| WO | WO 2018/237037 | 12/2018 |
| WO | WO 2019/000223 | 1/2019 |
| WO | WO 2019/133761 | 7/2019 |

OTHER PUBLICATIONS

Van Schooten et al (Lupus Science and Medicine, (Apr. 2019) vol. 6, Supp. Supplement 1, pp. A213. Abstract No. 293. Meeting Info: 13th International Congress on Systemic Lupus Erythematosus, LUPUS 2019. San Francisco, CA, United States. Apr. 5, 2019-Apr. 8, 2019).*

Buelow et al (Blood, (Nov. 13, 2019) vol. 134, No. Suppl. 1, p. 1874. Meeting Info.: 61st Annual Meeting and Exposition of the American-Society-of-Hematology (ASH). Orlando, FL, USA. Dec. 7-10, 2019. Amer Soc Hematol.).*

Li et al (Blood, (Nov. 5, 2020) vol. 136, Supp. Supplement 1, pp. 26-27. Meeting Info: 62nd ASH Annual Meeting. Virtual, Online. Dec. 5, 2020-Dec. 8, 2020).*

Rodrigez et al (Blood, (Nov. 5, 2020) vol. 136, Supp. Supplement 1, pp. 43-44. Meeting Info: 62nd ASH Annual Meeting. Virtual, Online. Dec. 5, 2020-Dec. 8, 2020).*

Adams et al., "Prolonged in Vivo Tumour Retention of a Human Diabody Targeting the Extracellular Domain of Human HER2/neu," (1998) British Journal of Cancer 77(9):1405-1412.

Ali et al., "T cells expressing an anti—B-cell maturation antigen chimeric antigen receptor cause remissions of multiple myeloma," (2016) Blood 128(13):1688-1700.

Anonymous, "Antibody Therapeutics—TeneoBio's Next Generation of Multispecific Antibody Therapeutics," (2018) retrieved from the Internet at: https://drug-dev.com/antibody-therapeutics-teneobios-next-generation-of-multispecifi-antibody-therapeutics/.

Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31(3):396-410.

Anonymous, "Flow Cytometry Antibody: CD3e Cat. No. CT026-R301, SinoBiological Inc,—Antibody-Catalogue," (2017) Sinobiological, Inc. Retrieved from Internet: URL http://www.sinobiologica.com/flow-cytometry-antibody-elite.html.

Arnett et al., "Crystal Structure of a Human CD3-epsilon/delta Dimer in Complex with a UCHT1 Single-chain Antibody Fragment," (2004) Proc Natl Acad Sci USA 101(46):16268-16273.

Baas et al., "Superhuman Mice," (2014) Science-Business eXchange 7(17):1-2.

Borchmann et al., "Phase 1 trial of the Novel Bispecific Molecule H22xKi-4 in Patients with Refractory Hodgkin Lymphoma," (2002) Blood 100(9):3101-3107.

Bruggemann et al., "Heavy-Chain-Only Antibody Expression and B-Cell Development in the Mouse," (2006) Crit. Rev. Immunol. 26(5):377-390.

Bruggemann et al., "Human Antibody Production in Transgenic Animals," (2014) Archivum Immunologiae et Therapiae Experimentalis, Birkhaeuser Verlag AG 63(2):101-108.

Buelow et al., "Development of a fully human T cell engaging bispecific antibody for the treatment of multiple myeloma," (2017) J Clin Oncol vol. 35 Supplement.

Carpenter et al., "B-cell Maturation Antigen Is a Promising Target for Adoptive T-cell Therapy of Multiple Myeloma," (2013) Clin Cancer Res 19(8):2048-2060.

Dai et al., "Chimeric Antigen Receptors Modified T-Cells for Cancer Therapy," (2016) J Natl Cancer Inst 108(7):dvj439.

Dooley et al., "Selection and Characterization of Naturally Occurring Single-domain (IgNAR) Antibody Fragments from Immunized Sharks by Phage Display," (2003) Molecular Immunology 40(1):25-33.

Desmyter et al., "Antigen Specificity and High Affinity Binding Provided by One Single Loop of a Camel Single-domain Antibody," (2001) Journal of Biological Chemistry, American Society for Biochemistry and Molecular Biology 276(28):26285-26290.

Durben et al., "Characterization of a Bispecific FLT3 X CD3 Antibody in an Improved, Recombinant Format for the Treatment of Leukemia," (2015) Molecular Therapy 23(4):648-655.

Force Aldred et al., "Winning the Numbers Game: Novel Multispecific Therapeutics from a Divers Collection of Human Domain Antibodies," (2016) retrieved from the Internet at: https://2019.lakepharma.com/files/symposiums/Winning%20the%20Numbers%20Game%20-%20Novel%20Multispecific%20Therapeuticsc%20from%20a%20Diverse%20Collection%20of%20Human%20Domain%20Antibodies%20-%20Shelley%20Force%20Aldred.pdf.

Frenken et al., Isolation of Antigen Specific Llama $V_{HH}$ Antibody Fragments and Their High Level Secretion by *Saccharomyces cerevisiae*, (2000) J. Biotechnol. 78:11-21.

Gershoni et al., "Epitope Mapping—The First Step in Developing Epitope-based Vaccines," (2007) Biodrugs, Adis International, Ltd. NZ 21(3):145-156.

Geurts et al., "Knockout Rats via Embryo Microinjection of Zinc-Finger Nucleases," (2009) Science 325(5939):433.

Ghahroudi et al., "Selection and Identification of Single Domain Antibody Fragments from Camel Heavy-chain Antibodies," (1997) FEBS Lett. 414:521-526.

(56) References Cited

OTHER PUBLICATIONS

Glennie et al., "Preparation and Performance of Bispecific F(ab' gamma)2 Antibody Containing Thioether-linked Fab' gamma Fragments," (1987) Journal of Immunology 139(7):2367-2375.
Gras et al., "BCMAp: an integral membrane protein in the Golgi apparatus of human mature B lymphocytes," (1995) Int. Immunol. 7(7):1093-1106.
Hamers-Casterman et al., "Naturally Occurring Antibodies Devoid of Light Chains," (1993) Nature 363:446-448.
Hipp et al., "A Novel BCMA/CD3 Bispecific T-cell Engager for the Treatment of Multiple Myeloma Induces Selective Lysis in Vitro and in Vivo," (2016) 31(8):1743-1751.
Hotzel et al., "A strategy for risk mitigation of antibodies with fast clearance," (2012) mABs 4(6):753-760.
Iri-Soffa et al., "Nanobody-based chimeric receptor gene integration in Jurkat cells mediated by PhiC31 integrase," (2011) Experimental Cell Research 317(18):2630-2641.
Jackson et al., "Driving Car T-cells forward," (2016) Nature Reviews Clinical Oncology 13:370—Jackson et al., "Driving CAR T-cells forward," (2016) Nature Reviews Clinical Oncology 13:370-383383.
Jamnani et al., "T cells expressing VHH-directed oligoclonal chimeric HER2 antigen receptors: Towards tumor-directed oligoclonal T cell therapy," (2014) Biochim Biophys Acta 1840(1):378-386.
Janssens et al., "Generation of Heavy-chain-only Antibodies in Mice," (2006) Proceedings of the National Academy of Sciences of the USA 103(41):15130-15135.
Jaton et al., "Recovery of antibody activity on reoxidation of completely reduced polyalanyl heavy chain and its Fd fragment derived from anti-2,4-dinitrophenyl antibody," (1968) Biochemistry 7(12):4185-4195.
Lefranc et al., "The Immunoglobulin FactsBook," Academic Press 2001.
Lindhofer et al., "Preferential Species-restricted Heavy/Light Chain Pairing in Rat/Mouse Quadromas. Implications for a Single-step Purification of Bispecific Antibodies," The Journal of Immunology, 155(1):219-225.
Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77:251-256.
Mack et al., "A Small Bispecific Antibody Construct Expressed as a Functional Single-chain Molecule with High Tumor Cell Cytotoxicity," (1995) PNAS 92:7021-7025.
Ménoret et al., "Transgenic Animals and Genetic Engineering Techniques," (2015) Transgenic Res 24:1079-1085.
Merchant et al., "An Efficient Route to Human Bispecific IgG," (1998) Nature Biotechnology, Gale Group, Inc. 16(7):677-684.
Muyldermans "Single domain camel antibodies: current status," (2001) J Biotechnol 74(4):277-302.
Nguyen et al., "Heavy-chain Only Antibodies Derived from Dromedary are Secreted and Displayed by Mouse B Cells," (2003) Immunology 109(1):93-101.
Nuttall et al., "Isolation and Characterization of an IgNAR Variable Domain Specific for the Human Mitochondrial Translocase Receptor Tom70," (2003) Eur. J. Biochem. 270:3543-3554.
Nuttall et al., "Selection and Affinity Maturation of IgNAR Variable Domains Targeting *Plasmodium falciparum* AMA1," (2004) Function and Bioinformatics 55:187-197.
Omniab: Naturally Optimized Human Antibodies (2016) retrieved from the Internet at: http://content.stockpr.com/omniab/db/252/746/file/OmniAb.pdf.
OMT Therapeutics Announces UniRat™ Alliance with Caltech, Business Wire (2015) retrieved from the Internet at: http://www.businesswire.com/news/home/20150514006523/en/OMT-Therapeutics-Announces-UniRat(TM)-Alliance-Caltech.
Revets et al., "Nanobodies as novel agents for cancer therapy," (2005) Expert Opin Biol Ther 5(1):111-124.

Ridgway et al., "'Knobs-into-holes' Engineering of Antibody CH3 Domains for Heavy Chain Heterodimerization," (1996) Protein Engineering 9(7):617-621.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):2341-2351.
Salmeron et al., "A conformational epitope expressed upon association of CD3-epsilon with either CD3-delta or CD3-gamma is the main target for recognition by anti-CD3 monoclonal antibodies." (1991) J. Immunol 147(9):3047-3052.
Sanz et al., "B cells as therapeutic targets in SLE" (2010) Nat Rev Rheumatol 6:326-337.
Sitia et al., "Developmental regulation of IgM secretion: the role of the carboxy-terminal cysteine," (1990) Cell 60(5):781-790.
Tai et al., "APRIL and BCMA promote human multiple myeloma growth and immunosuppression in the bone marrow microenvironment," (2016) Blood 127(25):3225-3236.
Tai et al., "Novel anti—B-cell maturation antigen antibody-drug conjugate (GSK2857916) selectively induces killing of multiple myeloma," (2014) Blood 123(20):3128-3138.
Trinklein et al., "Abstract LB-090: Sequence-based Discovery of Fully Human Anti-CD3 and Anti-PDL1 Single Domain Antibodies Using Novel Transgenic Rats," (2016) Cancer Research 76(14 Suppl).
Trinklein et al., "Efficient Tumor Killing and Minimal Cytokine Release with Novel T-cell Agonist Bispecific Antibodies," (2019) MABS 11 (4):639-652.
Van der Linden et al., "Comparison of Physical Chemical Properties of Llama VHH Antibody Fragments and Mouse Monoclonal Antibodies," (1999) Biochim. Biophys. Acta. 1431(1):37-46.
Weidle et al., "The Intriguing Options of Multispecific Antibody Formats for Treatment of Cancer," (2013) Cancer Genomics & Proteomics 10(1):1-18.
Wu et al., "Simultaneous Targeting of Multiple Disease Mediators by a Dual-variable-domain Immunoglobulin," (2007) Nature Biotechnology 25:1290-1297.
Yoon et al., "Both High and Low Avidity Antibodies to the T Cell Receptor can have Agonist Activity," (1994) Immunity 1(7):563-569.
Zou et al., "Heavy chain—only antibodies are spontaneously produced in light chain—deficient mice," (2007) J Exp Med 204(13):3271-3283.
PCT Application No. PCT/US2018/067755, filed Dec. 27, 2018 for TeneoBio, Inc.
Alderson et al., "CAT-8015: A Second-Generation Pseudomonas Exotoxin A—Based Immunotherapy Targeting CD22-Expressing Hematologic Malignancies," (2009) Clinical Cancer Research 15(3):832-839.
Almagro "Identification of differences in the specificity-determining residues of antibodies that recognize antigens of different size: implications for the rational design of antibody repertoires," (2004) Journal of Molecular Recognition 17(2):132-143.
Anonymous (TeneoBio, Inc.), "A Study of TNB-383B in Subjects with Relapsed or Refractory Multiple Myeloma," (2019) retrieved from the Internet on May 1, 2019 from URL:https://clinicaltrials.gov/ct2/show/NCT03933735, 4 pages.
Armitage, "A clinical evaluation of the International Lymphoma Study Group classification of non-Hodgkin's lymphoma," (1997) Blood 89(11):3909-3918.
Armour et al., "Recombinant human IgG molecules lacking Fcγ receptor I binding and monocyte triggering activities," (1999) Eur J Immunol. 29(8):2613-2624.
Buelow et al., "TNB3838.0001: A Multicenter, Phase 1, Open-Label, Dose-Escalation Andexpansion Study of TNB-3838, a Bispecific Antibodytargeting BCMA in Subjects with Relapsed or Refractorymultiple Myeloma," (2019) Blood 134(Supplement 1):1874.
Canfield et al., "The Binding Affinity of Human IgG for its High Affinity Fc Receptor Is Determined by Multiple Amino Acids in the CH2 Domain and Is Modulated by the Hinge Region," (1991) J. Exp. Med. 173:1483-1491.

(56) References Cited

OTHER PUBLICATIONS

Caraccio et al., "Bispecific Antibodies for Multiple Myeloma: A Review of Targets, Drugs, Clinical Trials and Future Directions," (2020) Frontiers in Immunology 11(50):1-25.
Chassaing et al., "Dextran Sulfate Sodium (DSS)-Inducted Colitis in Mice," (2014) Current Protocols in Immunology 15(25):1-14.
Chen et al., "Fusion protein linkers: Property, design and functionality ," (2013) Advanced Drug Delivery Reviews 65(10): 1357-1369.
Chini et al., "The Pharmacology of CD38/NADase: An Emerging Target in Cancer and Dieseases of Aging," (2018) Trends in Pharmacological Sciences 39(4):424-436.
Chothia et al., "Conformations of immunoglobulin hypervariable regions," (1989) Nature 342:877-883.
Chothia et al., "Canonical structures for the hypervariable regions of immunoglobulins," (1987) Journal of Molecular Biology 196(4):901-917.
Chou et al., "Quantitative Analysis of Dose-Effect Relationships: The Combined Effects of Multiple Drugs or Enzyme Inhibitors," (1984) Hopkins University School of Medicine 22:27-55.
Christian et al., "Measuring Bacterial Ectoenzyme Activities in Marine Waters Using Mercuric Chloride as a Preservative and Control," (1995) Marine Ecology Progress Series 123:217-224.
Clynes et al., "Fc Receptors are Required in Passie and Active Immunity to Melanoma," (1998) PNAS (USA) 95(2):652-656.
Concepcion et al., "Label-Free Detection of Biomolecular Interactions Using BioLayer Interferometry for Kinetic Characterization," (2009) Combinatorial Chemistry & High Throughput Screening 12(8):791-800.
Cui et al., "Targeted Integration in Rat and Mouse Embryos with Zinc-finger Nucleases," (2011) Nature Biotechnology 29(1):64-67.
DaSilva, "Abstract 34: A MET x MET bispecific antibody that induces receptor degradation potently inhibits the growth of MET-addicted tumor xenografts," (2017) AACR Annual Meeting 1-2.
DiLillo et al., "A BCMAxCD3 Bispecifi T Cell-engaging Antibody Demontstrates Robust Antitumor Efficacy Similar to that of Anti-BCMA CAR T Cells," (2020) Blood Advances 5(5):1291-1304.
Dimopoulos et al., "Daratumumab, Lenalidomide, and Dexamethasone for Multiple Myeloma," (2016) New England Journal of Medicine 375(14):1319-1331.
Dondelinger et al. "Understanding the Significance and Implications of Antibody Numbering and Antigen-binding Surface/Residue Definition," (2018) Frontiers in Immunology 9:1-15.
Duncan et al., "Localization of the binding site for the human high-affinity Fc receptor on IgG ," (1988) Nature 332:563-564.
Fry et al., "CD22-targeted CAR T Cells Induce Remission in B-ALL that is Naïve or Resistant to CD19-targeted CAR Immunotherapy," (2018) 24(1):20-28.
Gazzano-Santoro et al., "A non-radioactive complement-dependent cytotoxicity assay for anti-CD20 monoclonal antibody," (1996) Journal of Immunological Methods 202(2):163-171.
Giavridis et al., "CAR T cell-induced cytokine release syndrome is mediated by macrophages and abated by IL-1 blockade," (2018) Nature Medicine 24:731-738.
Gust et al., "Endothelial Activation and Blood—Brain Barrier Disruption in Neurotoxicity after Adoptive Immunotherapy with CD19 CAR-T Cells," (2017) Cancer Discovery 7(12):1405-1419.
Haffner et al., "Discovery, Synthesis, and Biological Evaluation of Thiazoloquin(az)olin(on)es as Potent CD38 Inhibitors," (2015) Jounral of Medical Chemistry 58:3548-3571.
Hamilton et al., "Humanization of Yeast to Produce Complex Terminally Sialylated Glycoproteins," (2006) Science 313(5792):1441-1443.
Hanes et al., "New advances in microsphere-based single-dose vaccines," (1997) Advanced Drug Delivery Reviews 28(1):97-119.
Hlavacek et al., "Steric Effects on Multivalent Ligand-Receptor Binding: Exclusion of Ligand Sites by Bound Cell Surface Receptors," (1999) Biophysical Journal 76(6):3031-3043.
Honegger and Plückthun, "Yet Another numbering scheme for immunoglobulin variable domains: an automatic modeling and analysis tool," (2001) Journal of Molecular Biology 309(3):657-670.
Jabbour et al., "Monoclonal Antibodies in Acute Lymphoblastic Leukemia," (2015) Blood 125(26):2010-2016.
Jemal et al., "Cancer Statistics, 2008," ACS Journals (2008) 58(2):71-96.
Kanda et al., "Establishment of a GDP-mannose 4,6-dehydratase (GMD) knockout host cell line: A new strategy for generating completely non-fucosylated recombinant therapeutics," (2007) Journal of Biotechnology 139:300-310.
Kaneko et al., "Anti-Inflammatory Activity of Immunoglobulin G Resulting from Fc Sialylation," (2006) Science 313(5787):670-673.
Kohler et al., "Continuous cultures of fused cells secreting antibody of predefined specificity," (1975) Nature 256:495-497.
Kumar et al., "Improved survival in multiple myeloma and the impact of novel therapies," (2008) Blood 111(5):2516-2520.
Kumar et al., "International Myeloma Working Group consensus criteria for response and minimal residual disease assessment in multiple myeloma," (2016) The Lancet Oncology 17(8):e328-e346.
Langer, "New Methods of Drug Delivery," (1990) Science 249(4976):1527-1533.
Lund et al., "Expression and characterization of truncated forms of humanized L243 IgG1," (2000) European Journal of Biochemistry 267(24):7246-7256.
Mariuzza et al., "The Structural Basis of Antigen-antibody Recognition," (1987) Ann Rev Biophys, Biophys Chem 16:139-159.
Menoret et al., "Characterization of Immunoglobulin Heavy Chain Knockout Rats," (2010) European Journal Immunology 40:2932-2941.
Mikkilineni et al., "Chimeric antigen receptor T-cell therapies for multiple myeloma," (2017) Blood 130(24):2594-2602.
Miller et al., "Design, Construction, and In Vitro Analyses of Multivalent Antibodies," (2003) Journal of Immunology 170(9):4854-4861.
Nishimoto et al., "Adoptive Therapy with Cord Blood T Regulatory Cells Enhances Anti-Myeloma Efficacy of T Cell Based Immunotherapies," (2020) Blood, vol. 136 Blood, Supplement 1, 2020, pp. 26-27.
Nguyen et al., "Functional Heavy-Chain Antibodies in Camelidae," (2001) Advances in Immunology 79:261-296.
Norelli et al., "Monocyte-derived IL-1 and IL-6 are differentially required for cytokine-release syndrome and neurotoxicity due to CAR T cells," (2018) Nature Medicine 24:739-748.
Ofran et al. "Automated identification of complementarity determining regions (CDRs) reveals peculiar characteristics of CDRs and B-cell epitopes," (2008) Journal of Immunology 181(9):6230-6235.
Padlan et al., "Identification of specificity-determining residues in antibodies," (1995) FASEB Journal 9(1):133-139.
Palumbo et al., "Daratumumab, Bortezomib, and Dexamethasone for Multiple Myeloma," (2016) New England Journal of Medicine 375(8):754-766.
Pick et al., "Daratumumab resistance is frequent in advanced-stage multiple myeloma patients irrespective of CD38 expression and is related to dismal prognosis," (2018) European Journal of Haematology 100(5):494-501.
Plückthun et al., "New protein engineering approaches to multivalent and bispecific antibody fragments," (1997) Immunology 3(2):83-105.
Presta et al., "Generation of a Humanized, High Affinity Anti-tissue Factor Antibody for Use as a Novel Antithrombotic Therapeutic," (2001) Thromb Haemost 85:379-389.
Presta et al., "Humanization of an antibody directed against IgE," (1993) Journal of Immunology 151:2623-2632.
Pulte et al., "CD39 Expression on T Lymphocytes Correlates with Severity of Disease in Patients With Chronic Lymphocytic Leukemia," (2011) Clinical Lymphoma, Myeloma & Leukemia 11(4):367-372.
Pulte et al., "Improvement in Survival of Older Adults with Multiple Myeloma: Results of an Updated Period Analysis of SEER Data," (2011) The Oncologist 16(11):1600-1603.

(56) References Cited

OTHER PUBLICATIONS

Qin et al., "Paralleled comparison of vectors for the generation of CAR-T cells," (2016) Anti-Cancer Drugs 27(8):711-722.

Rangaswamy, et al. "A Novel T-cell Bispecific Antibody Platform for Efficient T-cell Mediated Killing of Tumor Cells with Minimal Cytokine Oncology," (2018) Journal of Clinical Oncology 36(5) Supplement.

Ravetch et al., "Fc Receptors," (1991) Annual Review of Immunology 9:457-492.

Rodriguez et al., "Initial Results of a Phase I Study of TNB-383B, a BCMA x CD3 Bispecific T-Cell Redirecting Antibody, in Relapsed/Refractory Multiple Myeloma." Blood 2020; 136 (Supplement 1): 43-44.

Rouet et al., "Fully Human VH Single Domains That Rival the Stability and Cleft Recognition of Camelid Antibodies," (2015) Journal of Biological Chemistry 290(19):11905-11917.

Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.

Ryan et al., "Antibody Targeting of B-cell Maturation Antigen on Malignant Plasma Cells," (2007) Molecular Cancer Therapeutics 6(11):3009-3018.

Shallis et al., "The multi-faced potential of CD38 antibody targeting in multiple myeloma," (2017) Cancer Immunol Immunother 66:697-703.

Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem. 276(9):6591-6604.

Shoji-Hosaka et al., "Enhanced Fc-Dependent Cellular Cytotoxicity of Fc Fusion Proteins Derived from TNF Receptor II and LFA-3 by Fucose Removal from Asn-Linked Oligosaccharides," (2006) Journal of Biochemistry 140:777-783.

Tao et al., "Structural features of human immunoglobulin G that determine isotype-specific differences in complement activation," (1993) Journal of Experimental Medicine 178(2):661-667.

Tueresson et al., "Patterns of Improved Survival in Patients with Multiple Myeloma in the Twenty-First Century: A Population-Based Study," (2010) Journal of Clinical Oncology 28(5):830-834.

Van Schooten et al., "A novel CD3/Bcma bispecific antibody selectively kills plasma cells in bone marrow of healthy individuals with improved safety," (2019) Lupus Science & Medicine 6, Abstract 293.

Walker et al., "CD22: An Inhibitory Enigma," (2007) Immunology 123:314-325.

Waxman et al., "Racial disparities in incidence and outcome in multiple myeloma: a population-based study," (2010) Blood 116(25):5501-5506.

Werther et al., "Humanization of an anti-lymphocyte function-associated antigen (LFA)-1 monoclonal antibody and reengineering of the humanized antibody for binding to rhesus LFA-1," (1996) Journal of immunology 157:4986-4995.

Wu et al., "CD38-expressing macrophages drive age-related NAD+ decline," (2020) Nature Metabolism 2:1186-1187.

Zhao et al., "A germline knowledge based computational approach for determining antibody complementarity determining regions," (2010) Molecular Immunology 47(4):694-700.

U.S. Appl. No. 16/622,768, filed Jun. 20, 2018, 2020/0157232 (May 21, 2020), TeneoOne, Inc., Anti-BCMA Heavy Chain-Only Antibodies, Pending/Allowed.

U.S. Appl. No. 16/472,173, filed Jun. 20, 2019, 2019/0352412 (Nov. 21, 2019), TeneoBio, Inc., Anti-BCMA Heavy Chain-Only Antibodies, Pending/Allowed.

U.S. Appl. No. 16/622,881, filed Dec. 13, 2019, 2021/0147564 (May 20, 2021), TeneoBio, Inc., Anti-BCMA Heavy Chain-Only Antibodies, Pending.

U.S. Appl. No. 16/312,743, filed Jun. 20, 2019, 2019/0263904 (Aug. 29, 2019) TeneoBio, Inc., CD3 Binding Antibodies, Pending/Allowed.

U.S. Appl. No. 16/332,665, filed Mar. 12, 2019, 2020/0048348 (Feb. 13, 2020), TeneoBio, Inc., CD3 Binding Antibodies, Pending.

U.S. Appl. No. 17/308,946, filed May 5, 2021, 2021/0340255 (Nov. 4, 2021), TeneoOne, Inc., Multispecific Heavy Chain Antibodies With Modified Heavy Chain Constant Regions, Patented U.S. Pat. No. 11,186,639 (Nov. 30, 2021).

U.S. Appl. No. 17/347,553, filed Jun. 14, 2021, 2022/0089729 (Mar. 24, 2022), TeneoTwo, Inc., Multispecific Heavy Chain Antibodies With Modified Heavy Chain Constant Regions, Pending/Allowed.

U.S. Appl. No. 17/533,957, filed Nov. 23, 2021, TeneoOne, Inc., Multispecific Heavy Chain Antibodies With Modified Heavy Chain Constant Regions, Pending.

U.S. Appl. No. 16/958,105, filed Dec. 27, 2018, 2020/0339685 (Oct. 29, 2020), TeneoBio, Inc., CD3-Delta/Epsilon Heterodimer Specific Antibodies, Pending.

U.S. Appl. No. 16/327,299, filed Aug. 22, 2017, 2019/0225671 (Jul. 25, 2019), TeneoBio, Inc., Transgenic Non-Human Animals Producing Modified Heavy Chain-Only Antibodies, Pending.

U.S. Appl. No. 17/278,268, filed Sep. 20, 2019, 2021/0355215 (Nov. 18, 2021), TeneoBio, Inc., Methods for Purifying Heterodimeric, Multispecific Antibodies, Pending.

U.S. Appl. No. 17/244,785, filed Apr. 29, 2021, 2021/0403587 (Dec. 30, 2021), TeneoOne, Inc., Methods of Treating Multiple Myeloma, Pending.

U.S. Appl. No. 16/626,991, filed Dec. 27, 2019, 2020/0138865 (May 7, 2020) The United States of America,as represented by the Secretary,Department of Health and Human Services, Bethesda, MD (US); and TeneoBio, Inc., Anti-B-Cell Maturation Antigen Chimeric Antigen Receptors With Human Domains, Pending.

U.S. Appl. No. 16/956,502, filed Jun. 19, 2020, 2021/0095022 (Apr. 1, 2021), TeneoBio, Inc., Heavy Chain Antibodies Binding to CD22, Pending.

U.S. Appl. No. 17/288,485, filed Apr. 23, 2021, 2021/0388106 (Dec. 16, 2021), TeneoBio, Inc., Heavy Chain Antibodies Binding to CD38, Pending.

U.S. Appl. No. 17/260,213, filed Jan. 13, 2021, 2021/0332133 (Oct. 28, 2021), TeneoBio, Inc., Heavy Chain Antibodies Binding to CD19, Pending.

U.S. Appl. No. 17/601,417, filed Oct. 4, 2021, TeneoBio, Inc., Heavy Chain Antibodies Binding to PSMA, Pending.

U.S. Appl. No. 16/900,586, filed Jun. 12, 2020, 2021/0047402 (Feb. 18, 2021), TeneoBio, Inc., Mutlispecific Heavy Chain Antibodies Binding to CD22 and CD3, Pending.

* cited by examiner

FIG. 1A

| Internal ID | | CDR1 | CDR2 | CDR3 |
|---|---|---|---|---|
| 312557 | SEQ ID NO:1 | GFTFDDYA SEQ ID NO:29 | ISWNSGSI SEQ ID NO:24 | AKDSRGYGDYRLGGAY SEQ ID NO:41 |
| 308261 | SEQ ID NO:2 | GFTFDDYA SEQ ID NO:29 | ISWNSGSI SEQ ID NO:24 | AKDSRGYGDYRLGGAY SEQ ID NO:41 |
| 308159 | SEQ ID NO:3 | GFTFDDYA SEQ ID NO:29 | ISWNSGSI SEQ ID NO:24 | AKDSRGYGDYSRGGAY SEQ ID NO:42 |
| 308160 | SEQ ID NO:4 | GFTFDDYA SEQ ID NO:29 | ISWNSGSI SEQ ID NO:24 | AKDSRGYGDYSLGGAY SEQ ID NO:43 |
| 308256 | SEQ ID NO:5 | GFTFDDYA SEQ ID NO:29 | ISWNSGSI SEQ ID NO:24 | AKDSRGYGDYSLGGAY SEQ ID NO:43 |
| 312585 | SEQ ID NO:6 | GFTFANYA SEQ ID NO:30 | ISWNSGSI SEQ ID NO:24 | AKDSRGYGDYSRGGAY SEQ ID NO:42 |
| 312614 | SEQ ID NO:7 | GFTFNNYA SEQ ID NO:31 | ISWNSGSI SEQ ID NO:24 | AKDSRGYGDYSRGGAY SEQ ID NO:42 |
| 312583 | SEQ ID NO:8 | GFTFADYA SEQ ID NO:32 | ISWNSGSI SEQ ID NO:24 | AKDSRGYGDYSRGGAY SEQ ID NO:42 |
| 312586 | SEQ ID NO:9 | GFTFDNYA SEQ ID NO:33 | ISWNSGSI SEQ ID NO:24 | AKDSRGYGDYSRGGAY SEQ ID NO:42 |
| 312624 | SEQ ID NO:10 | GFTFDNYA SEQ ID NO:33 | ISWNSGSI SEQ ID NO:24 | AKDSRGYGDYSRGGAY SEQ ID NO:42 |
| 312578 | SEQ ID NO:11 | GFTFDDYA SEQ ID NO:29 | ISWNSGSI SEQ ID NO:24 | AKDSRGYGDYSRGGAY SEQ ID NO:42 |
| 312620 | SEQ ID NO:12 | GFTFDDYA SEQ ID NO:29 | ISWNSGSI SEQ ID NO:24 | AKDSRGYGSYSRGGAY SEQ ID NO:44 |
| 312634 | SEQ ID NO:13 | GFTFHNYA SEQ ID NO:34 | ISWNSGSI SEQ ID NO:24 | AKDSRGYGDYSLGGAY SEQ ID NO:43 |
| 312579 | SEQ ID NO:14 | GFTFDDYA SEQ ID NO:29 | ISWNSGSI SEQ ID NO:24 | AKDSRGYGDYSRGGAY SEQ ID NO:42 |
| 312630 | SEQ ID NO:15 | GFTFDNYA SEQ ID NO:33 | ISWNSGSI SEQ ID NO:24 | AKDSRGYGDYSLGGAY SEQ ID NO:43 |
| 312570 | SEQ ID NO:16 | GFTFDDYA SEQ ID NO:29 | ISWNSGSI SEQ ID NO:24 | AKDSRGYGDYRLGGAY SEQ ID NO:41 |
| 312567 | SEQ ID NO:17 | GFTFDDYA SEQ ID NO:29 | ISWNSGSI SEQ ID NO:24 | AKDSRGYGDYRLGGAY SEQ ID NO:41 |
| 312558 | SEQ ID NO:18 | GFTFDDYA SEQ ID NO:29 | ISWNSGSI SEQ ID NO:24 | AKDSRGYGDYRLGGAY SEQ ID NO:41 |

FIG. 1B

| 312325 | SEQ ID NO:19 | QSVSSN SEQ ID NO:35 | GAS SEQ ID NO:38 | QQYNNWPWT SEQ ID NO:45 |
|---|---|---|---|---|
| 308902-bivalent | SEQ ID NO:20 | GFTVSSYG SEQ ID NO:36 | IRGSDGST SEQ ID NO:39 | AKQGENDGPFDH SEQ ID NO:46 |
| 308902 | SEQ ID NO:21 | GFTVSSYG SEQ ID NO:36 | IRGSDGST SEQ ID NO:39 | AKQGENDGPFDH SEQ ID NO:46 |

FIG. 1C

| 304703 | SEQ ID NO:22 | GGSISSGGHY SEQ ID NO:37 | IHYSGST SEQ ID NO:40 | ARWRHDIFAAYPYYYYGMDV SEQ ID NO:47 |
|---|---|---|---|---|

| Column | 1 | 2 | 3 | 4 | 5 | 6 | 7 | 8 | 9 | 10 | 11 | 12 | 13 |
|---|---|---|---|---|---|---|---|---|---|---|---|---|---|
| | PARENTAL ANTI-CD3 ANTIBODY | | | ANTI-CD3:ANTI-BCMA BISPECIFIC ANTIBODY | | | | | | | | | |
| | anti-CD3 ID | Jurkat cell bind (MFI) | Cyno T-cell bind (MFI) | at BsAb dose ng/mL | IL-2 | IL-6 | IL-10 | IFNg | TNFa | Kill EC50 (ng/mL) | %Kill (333ng/mL) | KD (nM) | Jurkat cell bind (MFI) |
| | 312624 | 30.5 | 1.4 | CD3_F2E-BCMA | 130 | 1.0 | 241 | 705 | 1787 | 2.0 | 63 | 227 | 296 |
| | 312585 | 32.7 | 0.9 | CD3_F2C-BCMA | 93 | 0.5 | 19.2 | 751 | 1821 | 2.1 | 68 | 44 | 513 |
| | 312614 | 32.4 | 0.9 | CD3_F2D-BCMA | 294 | 1.5 | 89.9 | 1185 | 2387 | 6.1 | 63 | 86 | 357 |
| | 312634 | 21.4 | 1.1 | CD3_F2F-BCMA | 44 | 0.5 | 2.4 | 333 | 485 | 9.8 | 51 | 714 | 67 |
| | 312608 | 25.9 | 1.0 | CD3_F2A-BCMA | 96 | 0.5 | 3.3 | 505 | 1161 | 22.2 | 59 | 199 | 110 |
| | 312557 | 6.1 | 1.0 | CD3_F2B-BCMA | 8 | 0.5 | 0.6 | 154 | 553 | 150.1 | 38 | 1000 | 31 |
| | 312568 | 4.1 | 1.2 | CD3_F2G-BCMA | 1 | 0.5 | 0.5 | 49 | 231 | 352.0 | 12 | ND | 9 |
| | 304703 | 15.9 | 26.2 | CD3_F1A-BCMA | 212 | 0.8 | 48.5 | 746 | 1844 | 6.4 | 71 | 98 | 149 |

FIG. 3

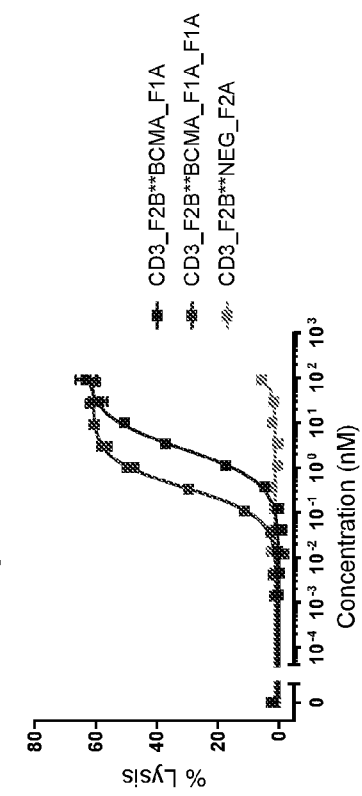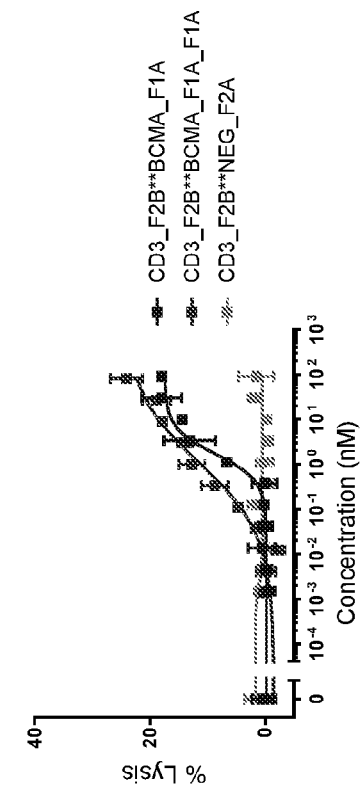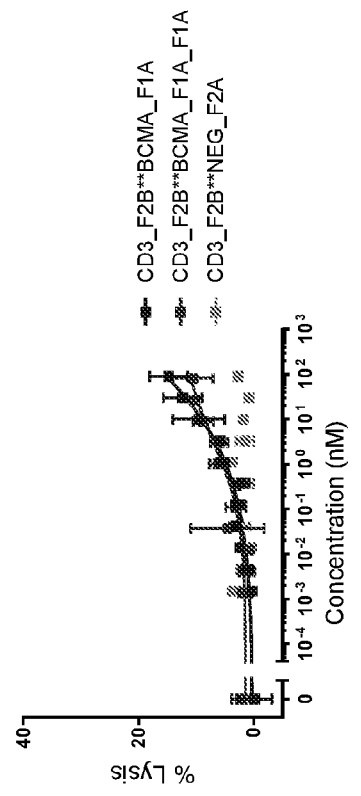
FIG. 8A RPMI-8226
FIG. 8B NCI-H929
FIG. 8C U-266
FIG. 8D K562

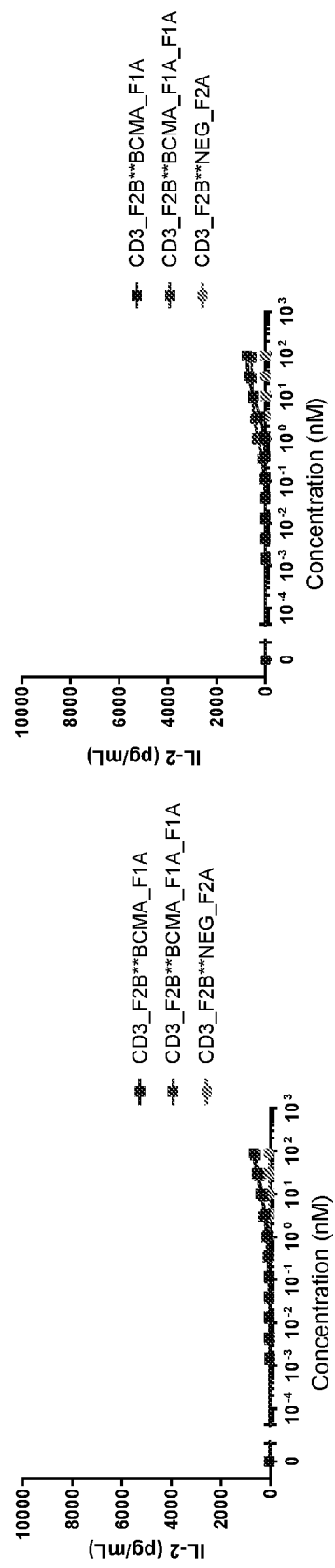
FIG. 9A RPMI-8226
FIG. 9B NCI-H929
FIG. 9C U-266
FIG. 9D K562

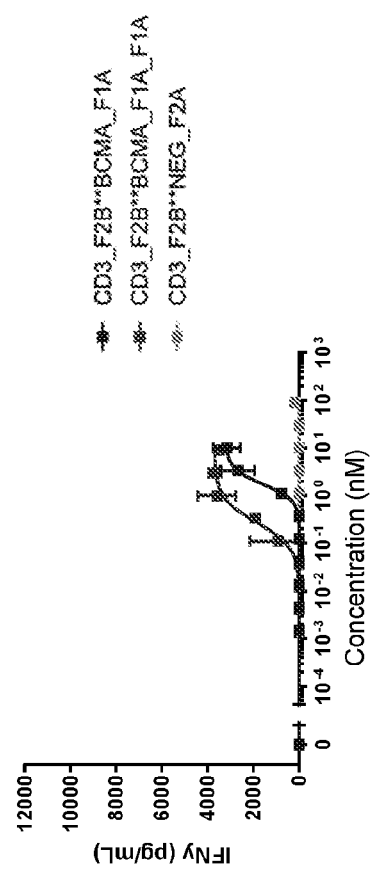
FIG. 10A RPMI-8226
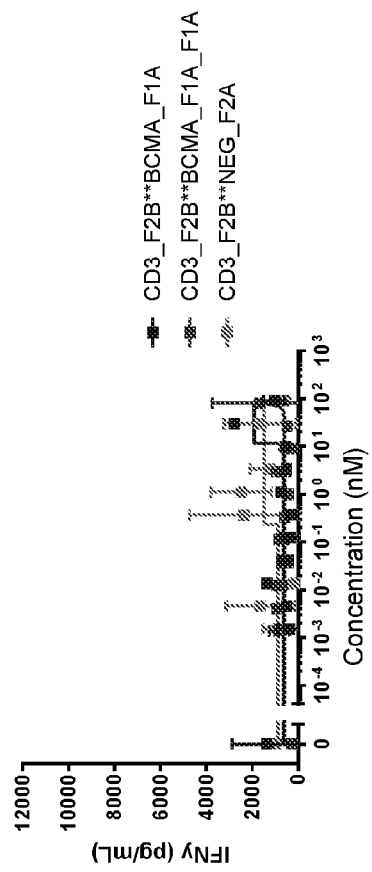
FIG. 10B NCI-H929
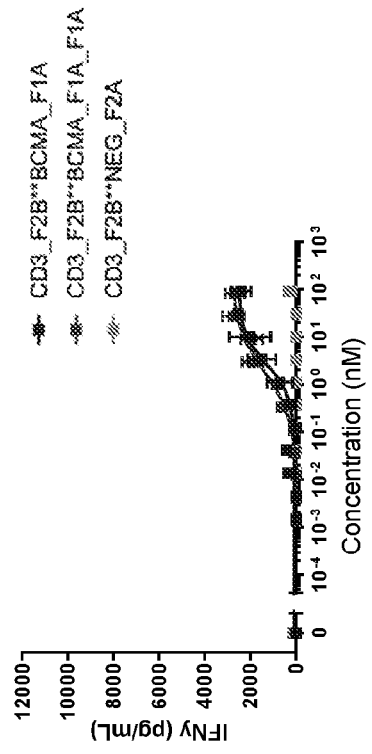
FIG. 10C U-266
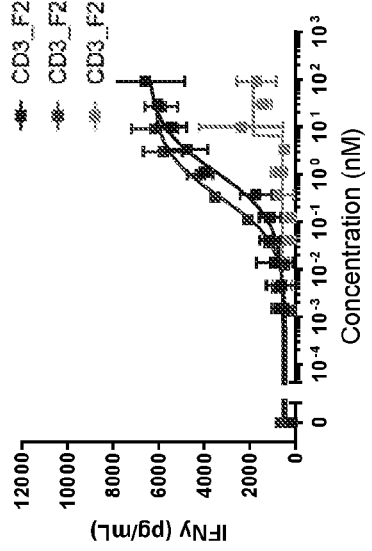
FIG. 10D K562

SEQUENCE LISTING

```
<160> NUMBER OF SEQ ID NOS: 48

<210> SEQ ID NO 1
<211> LENGTH: 123
<212> TYPE: PRT
<213> ORGANISM: Homo sapiens

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120

<210> SEQ ID NO 2
<211> LENGTH: 123
<212> TYPE: PRT
<213> ORGANISM: Homo sapiens

<400> SEQUENCE: 2
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120

<210> SEQ ID NO 3
<211> LENGTH: 123
<212> TYPE: PRT
<213> ORGANISM: Homo sapiens

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
        115                 120

<210> SEQ ID NO 4
<211> LENGTH: 123
<212> TYPE: PRT
<213> ORGANISM: Homo sapiens

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Pro Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser
        115                 120

<210> SEQ ID NO 5
<211> LENGTH: 123
<212> TYPE: PRT
<213> ORGANISM: Homo sapiens

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser
        115                 120

<210> SEQ ID NO 6
<211> LENGTH: 123
<212> TYPE: PRT
<213> ORGANISM: Homo sapiens

<400> SEQUENCE: 6

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ala Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
        115                 120

<210> SEQ ID NO 7
<211> LENGTH: 123
<212> TYPE: PRT
<213> ORGANISM: Homo sapiens
```

<400> SEQUENCE: 7

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Leu Tyr Tyr Cys
            85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
        115                 120
```

<210> SEQ ID NO 8
<211> LENGTH: 123
<212> TYPE: PRT
<213> ORGANISM: Homo sapiens

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
        115                 120
```

<210> SEQ ID NO 9
<211> LENGTH: 123
<212> TYPE: PRT
<213> ORGANISM: Homo sapiens

<400> SEQUENCE: 9

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60
```

Lys Gly Arg Phe Thr Ile Ser Arg Asp Asn Ala Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
            115                 120

<210> SEQ ID NO 10
<211> LENGTH: 123
<212> TYPE: PRT
<213> ORGANISM: Homo sapiens

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
            115                 120

<210> SEQ ID NO 11
<211> LENGTH: 123
<212> TYPE: PRT
<213> ORGANISM: Homo sapiens

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
            115                 120

<210> SEQ ID NO 12
<211> LENGTH: 123

```
<212> TYPE: PRT
<213> ORGANISM: Homo sapiens

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
            85                  90                  95

Ala Lys Asp Ser Arg Gly Tyr Gly Ser Tyr Ser Arg Gly Gly Ala Tyr
            100                 105                 110

Trp Gly Gln Gly Thr Leu Val Thr Val Ser Ser
        115                 120

<210> SEQ ID NO 13
<211> LENGTH: 123
<212> TYPE: PRT
<213> ORGANISM: Homo sapiens

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser
        115                 120

<210> SEQ ID NO 14
<211> LENGTH: 123
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
```

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                     85                  90                  95

Ala Lys Asp Ser Arg Gly Tyr Gly Asp Tyr Ser Arg Gly Gly Ala Tyr
                100                 105                 110

Cys Gly Gln Gly Thr Leu Val Thr Val Ser Ser
            115                 120

<210> SEQ ID NO 15
<211> LENGTH: 123
<212> TYPE: PRT
<213> ORGANISM: Homo sapiens

<400> SEQUENCE: 15

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asn Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                     85                  90                  95

Ala Lys Asp Ser Arg Gly Tyr Gly Asp Tyr Ser Leu Gly Gly Ala Tyr
                100                 105                 110

Trp Gly Gln Gly Thr Leu Val Thr Val Ser Ser
            115                 120

<210> SEQ ID NO 16
<211> LENGTH: 123
<212> TYPE: PRT
<213> ORGANISM: Homo sapiens

<400> SEQUENCE: 16

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                     85                  90                  95

Ala Lys Asp Ser Arg Gly Tyr Gly Asp Tyr Arg Leu Gly Gly Ala Tyr
                100                 105                 110

Trp Gly Gln Gly Thr Leu Val Thr Val Ser Ser
            115                 120
```

```
<210> SEQ ID NO 17
<211> LENGTH: 123
<212> TYPE: PRT
<213> ORGANISM: Homo sapiens

<400> SEQUENCE: 17

Glu Val Gln Leu Val Glu Ser Gly Gly Gly Leu Val Gln Pro Gly Arg
1               5                   10                  15

Ser Leu Arg Leu Ser Cys Glu Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120

<210> SEQ ID NO 18
<211> LENGTH: 123
<212> TYPE: PRT
<213> ORGANISM: Homo sapiens

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120

<210> SEQ ID NO 19
<211> LENGTH: 107
<212> TYPE: PRT
<213> ORGANISM: Homo sapiens

<400> SEQUENCE: 19

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45
```

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Trp
                 85                  90                  95

Thr Phe Gly Gln Gly Thr Lys Val Glu Ile Lys
                100                 105

<210> SEQ ID NO 20
<211> LENGTH: 243
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Val Ser Ser Tyr
                20                  25                  30

Gly Met Ser Trp Val Arg Gln Ala Pro Gly Lys Gly Pro Glu Trp Val
             35                  40                  45

Ser Gly Ile Arg Gly Ser Asp Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Gly Glu Asn Asp Gly Pro Phe Asp His Arg Gly Gln Gly
                100                 105                 110

Thr Leu Val Thr Val Ser Ser Gly Gly Gly Ser Glu Val Gln Leu
            115                 120                 125

Leu Glu Ser Gly Gly Gly Leu Val Gln Pro Gly Gly Ser Leu Arg Leu
        130                 135                 140

Ser Cys Ala Ala Ser Gly Phe Thr Val Ser Ser Tyr Gly Met Ser Trp
145                 150                 155                 160

Val Arg Gln Ala Pro Gly Lys Gly Pro Glu Trp Val Ser Gly Ile Arg
                165                 170                 175

Gly Ser Asp Gly Ser Thr Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Lys Gln Gly
    210                 215                 220

Glu Asn Asp Gly Pro Phe Asp His Arg Gly Gln Gly Thr Leu Val Thr
225                 230                 235                 240

Val Ser Ser

<210> SEQ ID NO 21
<211> LENGTH: 119
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
 1               5                   10                  15

```
Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser
        115
```

```
<210> SEQ ID NO 22
<211> LENGTH: 128
<212> TYPE: PRT
<213> ORGANISM: Homo sapiens

<400> SEQUENCE: 22

Gln Leu Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile His Tyr Ser Gly Ser Thr Tyr Tyr Asn Pro Ser
 50                  55                  60

Leu Lys Ser Arg Val Ile Ile Ser Val Asp Thr Ser Lys Asn Gln Phe
 65                  70                  75                  80

Ser Leu Lys Leu Arg Ser Val Thr Ala Ala Asp Thr Ala Val Tyr Tyr
                85                  90                  95

Cys Ala Arg Trp Arg His Asp Ile Phe Ala Ala Tyr Pro Tyr Tyr Tyr
            100                 105                 110

Tyr Gly Met Asp Val Trp Gly Gln Gly Thr Leu Val Thr Val Ser Ser
        115                 120                 125
```

```
<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid

<400> SEQUENCE: 23

Gly Phe Thr Phe Xaa Xaa Tyr Ala
 1               5
```

```
<210> SEQ ID NO 24
<211> LENGTH: 8
<212> TYPE: PRT
<213> ORGANISM: Homo sapiens

<400> SEQUENCE: 24
```

```
Ile Ser Trp Asn Ser Gly Ser Ile
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid

<400> SEQUENCE: 25

Ala Lys Asp Ser Arg Gly Tyr Gly Xaa Tyr Xaa Xaa Gly Gly Ala Tyr
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Any amino acid

<400> SEQUENCE: 26

Ala Lys Asp Ser Arg Gly Tyr Gly Asp Tyr Xaa Xaa Gly Gly Ala Tyr
1               5                   10                  15

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Val Ala Ala Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ser Thr Lys Gly Pro
1               5

<210> SEQ ID NO 29
<211> LENGTH: 8
<212> TYPE: PRT
<213> ORGANISM: Homo sapiens

<400> SEQUENCE: 29
```

```
Gly Phe Thr Phe Asp Asp Tyr Ala
1               5

<210> SEQ ID NO 30
<211> LENGTH: 8
<212> TYPE: PRT
<213> ORGANISM: Homo sapiens

<400> SEQUENCE: 30

Gly Phe Thr Phe Ala Asn Tyr Ala
1               5

<210> SEQ ID NO 31
<211> LENGTH: 8
<212> TYPE: PRT
<213> ORGANISM: Homo sapiens

<400> SEQUENCE: 31

Gly Phe Thr Phe Asn Asn Tyr Ala
1               5

<210> SEQ ID NO 32
<211> LENGTH: 8
<212> TYPE: PRT
<213> ORGANISM: Homo sapiens

<400> SEQUENCE: 32

Gly Phe Thr Phe Ala Asp Tyr Ala
1               5

<210> SEQ ID NO 33
<211> LENGTH: 8
<212> TYPE: PRT
<213> ORGANISM: Homo sapiens

<400> SEQUENCE: 33

Gly Phe Thr Phe Asp Asn Tyr Ala
1               5

<210> SEQ ID NO 34
<211> LENGTH: 8
<212> TYPE: PRT
<213> ORGANISM: Homo sapiens

<400> SEQUENCE: 34

Gly Phe Thr Phe His Asn Tyr Ala
1               5

<210> SEQ ID NO 35
<211> LENGTH: 6
<212> TYPE: PRT
<213> ORGANISM: Homo sapiens

<400> SEQUENCE: 35

Gln Ser Val Ser Ser Asn
1               5

<210> SEQ ID NO 36
<211> LENGTH: 8
<212> TYPE: PRT
<213> ORGANISM: Homo sapiens

<400> SEQUENCE: 36

Gly Phe Thr Val Ser Ser Tyr Gly
1               5
```

<210> SEQ ID NO 37
<211> LENGTH: 10
<212> TYPE: PRT
<213> ORGANISM: Homo sapiens

<400> SEQUENCE: 37

Gly Gly Ser Ile Ser Ser Gly Gly His Tyr
1               5                   10

<210> SEQ ID NO 38
<211> LENGTH: 3
<212> TYPE: PRT
<213> ORGANISM: Homo sapiens

<400> SEQUENCE: 38

Gly Ala Ser
1

<210> SEQ ID NO 39
<211> LENGTH: 8
<212> TYPE: PRT
<213> ORGANISM: Homo sapiens

<400> SEQUENCE: 39

Ile Arg Gly Ser Asp Gly Ser Thr
1               5

<210> SEQ ID NO 40
<211> LENGTH: 7
<212> TYPE: PRT
<213> ORGANISM: Homo sapiens

<400> SEQUENCE: 40

Ile His Tyr Ser Gly Ser Thr
1               5

<210> SEQ ID NO 41
<211> LENGTH: 16
<212> TYPE: PRT
<213> ORGANISM: Homo sapiens

<400> SEQUENCE: 41

Ala Lys Asp Ser Arg Gly Tyr Gly Asp Tyr Arg Leu Gly Gly Ala Tyr
1               5                   10                  15

<210> SEQ ID NO 42
<211> LENGTH: 16
<212> TYPE: PRT
<213> ORGANISM: Homo sapiens

<400> SEQUENCE: 42

Ala Lys Asp Ser Arg Gly Tyr Gly Asp Tyr Ser Arg Gly Gly Ala Tyr
1               5                   10                  15

<210> SEQ ID NO 43
<211> LENGTH: 16
<212> TYPE: PRT
<213> ORGANISM: Homo sapiens

<400> SEQUENCE: 43

Ala Lys Asp Ser Arg Gly Tyr Gly Asp Tyr Ser Leu Gly Gly Ala Tyr
1               5                   10                  15

```
<210> SEQ ID NO 44
<211> LENGTH: 16
<212> TYPE: PRT
<213> ORGANISM: Homo sapiens

<400> SEQUENCE: 44

Ala Lys Asp Ser Arg Gly Tyr Gly Ser Tyr Ser Arg Gly Gly Ala Tyr
1               5                   10                  15

<210> SEQ ID NO 45
<211> LENGTH: 9
<212> TYPE: PRT
<213> ORGANISM: Homo sapiens

<400> SEQUENCE: 45

Gln Gln Tyr Asn Asn Trp Pro Trp Thr
1               5

<210> SEQ ID NO 46
<211> LENGTH: 12
<212> TYPE: PRT
<213> ORGANISM: Homo sapiens

<400> SEQUENCE: 46

Ala Lys Gln Gly Glu Asn Asp Gly Pro Phe Asp His
1               5                   10

<210> SEQ ID NO 47
<211> LENGTH: 20
<212> TYPE: PRT
<213> ORGANISM: Homo sapiens

<400> SEQUENCE: 47

Ala Arg Trp Arg His Asp Ile Phe Ala Ala Tyr Pro Tyr Tyr Tyr Tyr
1               5                   10                  15

Gly Met Asp Val
            20

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Arg or Ser
<220> FEATURE:
<221> NAME/KEY: MOD_RES
<222> LOCATION: (12)..(12)
<223> OTHER INFORMATION: Leu or Arg

<400> SEQUENCE: 48

Ala Lys Asp Ser Arg Gly Tyr Gly Asp Tyr Xaa Xaa Gly Gly Ala Tyr
1               5                   10                  15
```

CD3 BINDING ANTIBODIES

CROSS REFERENCE

This application is a divisional application of U.S. application Ser. No. 16/332,665, filed Mar. 12, 2019, which is a US National Stage entry under 35 USC 371 of PCT Application No. PCT/US2017/038377, filed Jun. 20, 2017, which claims the benefit of U.S. Provisional Application No. 62/491,908, filed Apr. 28, 2017 and also claims the benefit of U.S. Provisional Application No. 62/394,360, filed Sep. 14, 2016, the full disclosures of which are all hereby incorporated by reference herein in their entireties.

SEQUENCE LISTING

The instant application contains a Sequence Listing which has been filed electronically in ASCII format and is hereby incorporated by reference in its entirety. Said ASCII copy, created on Feb. 10, 2020, is named TNO-0010-US2_SL.txt and is 30,557 bytes in size.

BACKGROUND

The body's immune system serves as a defense against infection, injury and cancer. Two separate but interrelated systems, humoral and cellular immune systems, work together to protect the body. The humoral system is mediated by soluble factors, named antibodies, which neutralize products recognized as being foreign by the body. In contrast, the cellular system involves cells, such as T cells and macrophages, which remove and neutralize foreign invaders.

The activation of T cells is critical for the stimulation of immune responses. T cells exhibit immunological specificity and direct most of the cellular immune responses. Although T cells do not secrete antibodies, they are required for the secretion of antibodies by B lymphocytes. T cell activation requires the participation of a number of cell surface molecules, such as the T cell receptor complex, and CD4 or CD8 molecules. The antigen-specific T cell receptor (TcR) is composed of a disulfide-linked heterodimer, membrane glycoprotein with chains, alpha and beta ($\alpha$ and $\beta$), or gamma and delta ($\gamma$ and $\delta$). The TcR is non-covalently linked with a complex of invariant proteins, designated CD3.

T cells are known to exert potent antitumor effects in numerous experimental settings. Antibodies capable of effectively recruiting T cells against tumor cells have been available as bispecific antibodies, for example directed to tumor-associated antigens (TAAs) and agonistic T-cell membrane proteins, such as the TCR/CD3 complex and CD28. These bispecific antibodies are capable of activating T cells, irrespective of their TCR specificity, resulting in specific lysis of cells carrying the respective TAAs.

However, while anti-CD3 bispecific antibodies can redirect T-cell-mediated lysis toward malignant cells, clinical trials with CD3-based bsAbs have shown high toxicity in patients. Non-specific T-cell activation from bsAbs can occur in an antigen-independent manner due to the Fc/Fc receptor (FcR) interaction, or in an antigen-dependent manner when antigen is expressed on both normal and tumor cells. Both mechanisms may have been responsible for the toxicity observed in prior clinical studies. (See for example, Link et al. (1998) Int. J. Cancer 77(2):251-6; Durben et al. *Molecular Therapy* (2015); 23 4, 648-655). Because of the resulting cytokine release syndrome, there have been significant blocks to the development of these antibodies for therapeutic purposes.

The interaction of the T cell receptor (TCR) with its peptide-MHC ligand determines the activity of a T cell. The binding characteristics of this interaction has been studied in great detail and shown to control T cell function. The strength and nature of the TCR-peptide/MHC interaction determines whether T cells exert effector functions or are inactivated and deleted. Antibodies against CD3 activate T cells by changing the conformation of the CD3ε chain and depending on the epitope may have either agonistic or antagonistic effects on T cells (Yoon et al., 1994 Immunity 1:563-569). In light of the significant side-effects of many T cell agonists it may be preferred to maintain potent anti-tumor effects while reducing the release of pro-inflammatory cytokines. However, partial agonistic anti-CD3 antibodies may alter the CD3ε chain sub-optimally resulting in ineffective signaling, and most anti-CD3 antibodies are full agonists for both pathways. It is unclear whether these effector functions can be separated. Many existing anti-CD3 antibodies (for example SP-34, UCHT1, OKT3) have affinities in the range of 1-50 nM KD, however this may not be optimal for therapeutic use.

CD3 specific antibodies, and bispecific antibodies derived therefrom are provided by the invention.

PUBLICATIONS

CD3 antibodies are disclosed, for example, in U.S. Pat. Nos. 5,585,097; 5,929,212; 5,968,509; 6,706,265; 6,750,325; 7,381,803; 7,728,114. Bispecific antibodies with CD3 binding specificity are disclosed, for example, in U.S. Pat. Nos. 7,262,276; 7,635,472; 7,862,813; and 8,236,308, each herein specifically incorporated by reference.

SUMMARY

Compositions and methods of use thereof are provided for a family of closely related antibodies that bind to and activate signaling through CD3, e.g. activation of CD3$^+$ T cells. The antibody family comprises a set of CDR sequences as defined herein. The family of antibodies provides a number of benefits that contribute to utility as clinically therapeutic agent(s). The antibodies within the family include members with a range of binding affinities, allowing the selection of a specific sequence with a desired affinity. The ability to fine tune affinity is of particular importance to manage the level of CD3 activation in an individual being treated, and thereby reduce toxicity.

In some embodiments, anti-CD3 antibodies have an affinity (KD) for CD3 ranging from around about $10^{-6}$ to around about $10^{-11}$. Anti-CD3 antibodies that have affinities (KD) of 50 nM or greater, 100 nM or greater, 500 nM or greater, or 1 µM or greater can be desirable to more closely mimic the TCR/MHC interaction and minimize toxic cytokine release while maintaining effective tumor cell lysis. In some embodiments, anti-CD3 antibodies are characterized or selected for reduced propensity to induce cytokine release, upon binding to a competent T cell, e.g. for release of IL-2 and IFNγ. Antibodies may be selected for therapeutic use that optimize killing of tumor cells and reduced release of cytokines, e.g. an antibody that, within the family of antibody sequences described herein, induces a cytokine release that is less than about half the maximum observed for a family member in a comparative assay, and may be less, e.g. less and about 25% the maximum observed for a family member in a comparative assay. In some embodiments, bispecific or multispecific antibodies are provided, which comprise at least a heavy chain variable region from the antibody family and may comprise a heavy and light chain variable region provided herein. Bispecific antibodies comprise at least the heavy chain variable region of an antibody specific for a protein other than CD3, and may comprise a heavy and light chain variable region. In some such embodiments, the second antibody specifically binds to a tumor associated antigen, a targeting antigen, e.g. integrins, etc., a pathogen antigen, a checkpoint protein, and the like. Various formats of bispecific antibodies are within the ambit of the invention, including without limitation single chain polypeptides, two chain polypeptides, three chain polypeptides, four chain polypeptides, and multiples thereof.

Each of the CD3 specific antibodies comprises a VH domain, comprising CDR1, CDR2 and CDR3 sequences in a human VH framework. The family 2 CDR sequences may be situated, as an example, in the region of around amino acid residues 26-33; 51-58; and 97-112 for CDR1, CDR2 and CDR3, respectively, of the provided exemplary variable region sequences set forth in SEQ ID NO: 1-18. It will be understood by one of skill in the art that the CDR sequences may be in different position if a different framework sequence is selected, although generally the order of the sequences will remain the same.

The CDR sequences for a family 2 antibody may have the following sequence formulas. An X indicates a variable amino acid, which may be specific amino acids as indicated below.

CDR1
$G_1\ F_2\ T_3\ F_4\ X_5\ X_6\ Y_7\ A_8$ where:

$X_5$ may be any amino acid; in some embodiments $X_5$ is D, A or H; in some embodiments $X_5$ is D.

$X_6$ may be any amino acid; in some embodiments $X_6$ is D or N; in some embodiments $D_6$ is D.

In some embodiments a CDR1 sequence of a family 2 anti-CD3 antibody comprises the sequence set forth in any of SEQ ID NO:1-18, residues 26-33.

CDR2
$I_1,\ S_2,\ W_3,\ N_4,\ S_5,\ G_6,\ S_7,\ I_8,$

In some embodiments a CDR2 sequence of a family 2 anti-CD3 antibody comprises the sequence set forth in any of SEQ ID NO: 1-18, residues 51-58.

CDR3
$A_{1\prime\prime}\ K_{2\prime\prime}\ D_{3\prime\prime}\ S_{4\prime\prime}\ R_{5\prime\prime}\ G_{6\prime\prime}\ Y_{7\prime\prime}\ G_{8\prime\prime}\ X_{9\prime\prime}\ Y_{10\prime\prime}\ X_{11\prime\prime}\ X_{12\prime\prime}\ G_{13\prime\prime}\ G_{12\prime\prime}\ A_{15\prime\prime}\ Y_{16\prime\prime}$ where:

$X_{9\prime\prime}$ may be any amino acid, in some embodiments $X_{9\prime\prime}$ is D or S; in some embodiments $X_{9\prime\prime}$ is D;

$X_{11\prime\prime}$ may be any amino acid; in some embodiments $X_{11\prime\prime}$ is R or S;

$X_{12\prime\prime}$ may be any amino acid; in some embodiments $X_{12\prime\prime}$ is L or R.

In some embodiments a CD3 sequence of a family 2 anti-CD3 antibody has the formula A K D S R G Y G D Y $X_{11\prime\prime}\ X_{12\prime\prime}$ G G A Y where $X_{11\prime\prime}$ and $X_{12\prime\prime}$ are as defined above. In some embodiments a CDR3 sequence of a family 2 anti-CD3 antibody comprises the sequence set forth in any of SEQ ID NO: 1-18, residues 97-112. In some embodiments the CD3-binding VH domain of a family 2 antibody is paired with a light chain variable region domain. In some such embodiments the light chain is a fixed light chain.

In some embodiments the light chain comprises a VL domain with CDR1, CDR2 and CDR3 sequences in a human VL framework. The CDR sequences may be those of SEQ ID NO:19. In some embodiments, the CDR1 sequence comprises amino acid residues 27-32; 50-52; 89-97 for CDR1, CDR2, CDR3, respectively.

In some embodiments the CDR sequences of an antibody of the invention are a sequence with at least 85% identity, at least 90% identity, at least 95% identity, at least 99% identity relative to a CDR sequence or set of CDR sequences in SEQ ID NO: 1-18. In some embodiments a CDR sequence of the invention comprises one, two, three or more amino acid substitutions relative to a CDR sequence or set of CDR sequences in any one of SEQ ID NO: 1-18. In some embodiments said amino acid substitution(s) are one or more of position 5 or 10 of CDR1, position 2, 6 or 7 of CDR2, position 1, 8, 9 or 10 of CDR3, relative to the family 2 formulas provided above.

In some embodiments, a bispecific antibody of the invention comprises a CD3-binding variable region described herein, paired with a light chain. In some embodiments the light chain comprises the variable region sequence set forth in SEQ ID NO:19, or a variable region comprising the set of CDR sequences in SEQ ID NO:19 and framework sequences. Various Fc sequences find use, including without limitation human IgG1, IgG2a, IgG2b, IgG3, IgG4, etc. In some embodiments, the second arm of the bispecific antibody comprises a variable region that specifically binds to a tumor-associated antigen. In some embodiments, the second arm of the bispecific antibody comprises a variable region that specifically binds to BCMA. In some embodiments the anti-BCMA arm is a single chain variable region, for example as shown in FIG. 2B. In some embodiments the anti-BCMA arm comprises the variable region sequence set forth in SEQ ID NO:20; or the tandem variable region sequence set forth in SEQ ID NO:21. The Fc sequence of the anti-BCMA arm may be, without limitation, human IgG1, IgG2a, IgG2b, IgG3, IgG4, etc. The CDR sequences may be those contained in SEQ ID NO:20. In some embodiments, the CDR sequence comprises amino acid residues 26-33; 51-58; 97-108 for CDR1, CDR2, CDR3, respectively.

In other embodiments, pharmaceutical compositions are provided, comprising at least a CD3-binding VH domain of the invention, e.g. a monospecific, bispecific, etc. antibody or antibody-like protein comprising at least a CD3-binding VH domain of the invention; and a pharmaceutically acceptable excipient. The composition may be lyophilized, suspended in solution, etc. and may be provided in a unit dose formulation.

In some embodiments, a method is provided for treatment of cancer, the method comprising administering to an individual in need thereof an effective dose of a monospecific, bi-specific, etc. antibody of the invention. Where the antibody is bispecific, a second antigen-binding site may specifically bind a tumor antigen, a checkpoint protein, etc. In various embodiments, the cancer is selected from the group consisting of ovarian cancer, breast cancer, gastrointestinal, brain cancer, head and neck cancer, prostate cancer, colon cancer, lung cancer, leukemia, lymphoma, sarcoma, carcinoma, neural cell tumors, squamous cell carcinomas, germ cell tumors, metastases, undifferentiated tumors, seminomas, melanomas, myelomas, neuroblastomas, mixed cell tumors, and neoplasias caused by infectious agents.

In some embodiments, a method is provided for treatment of infectious disease, the method comprising administering to an individual in need thereof an effective dose of a monospecific, bi-specific, etc. antibody of the invention. Where the antibody is bispecific, a second antigen-binding site may specifically bind a pathogen antigen, e.g. bacteria, viruses or parasites.

In other embodiments, a method is provided for the production of a bispecific antibody of the present invention comprising expressing the antibody sequences, e.g. one or more light chain encoding sequences, one or more heavy chain encoding sequences, in a single host cell. In various embodiments, the host cell may be a prokaryotic or an eukaryotic cell, such as a mammalian cell.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1C. FIG. 1A shows an alignment of CDR1, 2 and 3 regions of members of antibody family 2 of SEQ ID NO:1-18, which specifically bind to human CD3, corresponding to residues 26-33; 51-58; and 97-112. FIG. 1B shows the CDR1, 2 and 3 regions of the fixed light chain (SEQ ID NO:19); and an exemplary anti-BCMA sequence (SEQ ID NO:20 and SEQ ID NO:21). FIG. 1C provides the CDR sequences of a reference anti-CD3 antibody (SEQ ID NO:22), ID 304704.

FIG. 2A anti-CD3:anti-tumor-antigen bispecific antibody with common light chain (3 total unique chains). FIG. 2B anti-CD3:anti-tumor-antigen bispecific antibody with 2 unique light chains (4 total unique chains). FIG. 2C anti-CD3:anti-tumor-antigen bispecific antibody with heavy-chain only tumor antigen binding domain chain (3 unique chains). FIG. 2D anti-CD3:anti-tumor-antigen bispecific antibody with scFv tumor antigen binding domain (3 total unique chains). FIG. 2E anti-CD3:anti-tumor-antigen bispecific antibody with scFv anti-CD3 binding domain (3 total unique chains)

FIG. 3. Anti-CD3 family 2 data table summarizes the behavior of anti-CD3 antibodies in monospecific and bispecific format. Column 1 shows the sequence ID for the anti-CD3 VH sequence. Column 2 shows the MFI value for Jurkat cell binding of the parental monospecific anti-CD3. Column 3 shows the MFI value for cyno T-cell binding of the parental monospecific anti-CD3. Column 4 shows the name of the aCD3:aBCMA bispecific antibody. Column 5 shows the picograms of IL-2 released by pan T-cells stimulated by the bispecific antibody binding the BCMA protein coated on plastic at the dose indicated. Column 6 shows the picograms of IL-6 released by pan T-cells stimulated by the bispecific antibody binding the BCMA protein coated on plastic at the dose indicated. Column 7 shows the picograms of IL-10 released by pan T-cells stimulated by the bispecific antibody binding the BCMA protein coated on plastic at the dose indicated. Column 8 shows the picograms of IFN-γ released by pan T-cells stimulated by the bispecific antibody binding the BCMA protein coated on plastic at the dose indicated. Column 9 shows the picograms of TNFα released by pan T-cells stimulated by the bispecific antibody binding the BCMA protein coated on plastic at the dose indicated. Column 10 shows the $EC_{50}$ of bispecific antibody-mediated U266 tumor cell lysis in presence of human pan T-cells. Column 11 shows the percent lysis of U266 tumor cells in the presence of bispecific antibody and human pan T-cells at a dose of 333 ng/mL of bispecific antibody. Column 12 shows the protein binding affinity of the anti-CD3 arm of the bispecific antibody measured by Octet®. Column 13 shows the MFI value for Jurkat cell binding of the bispecific antibody.

FIG. 8A-8D. Bispecific antibody-mediated tumor cell lysis. αCD3_F1F:aBCMA bispecific antibodies were assayed for the ability to kill three different BCMA+ tumor cells and one BCMA-negative cell line through redirection of activated primary T cells. In this experiment, tumor cells were mixed with activated pan T-cells in a 10:1 E:T ratio along with the addition of bispecific antibody. FIG. 8A shows killing of RPMI-8226 cells, FIG. 8B shows killing of NCI-H929 cells, FIG. 8C shows killing of U-266 cells, and FIG. 8D shows killing of K562 cells, a negative control. The x-axis shows the concentration of antibody used and the y-axis shows the % lysis of tumor cells 6 hours after addition of antibody.

FIG. 9A-9D. Bispecific antibody-mediated IL-2 release. The level of IL-2 cytokine release was measured after resting human T cells were cultured with various tumor cell lines and increasing doses of αCD3_F1F:aBCMA bispecific antibody. FIG. 9A shows IL-2 release stimulated by RPMI-8226 cells, FIG. 9B shows IL-2 release stimulated by NCI-H929 cells, FIG. 9C shows IL-2 release stimulated by U-266 cells, and FIG. 9D shows IL-2 release stimulated by K562 cells, a negative control.

FIG. 10A-10D. Bispecific antibody-mediated IFN-γ release. The level of IFN-γ cytokine release was measured after resting human T cells were cultured with various tumor cell lines and increasing doses of αCD3_F1F:aBCMA bispecific antibody. FIG. 10A shows IFN-γ release stimulated by RPMI-8226 cells, FIG. 10B shows IFN-γ release stimulated by NCI-H929 cells, FIG. 10C shows IFN-γ release stimulated by U-266 cells, and FIG. 10D shows IFN-γ release stimulated by K562 cells, a negative control.

DETAILED DESCRIPTION

Figure 2A:
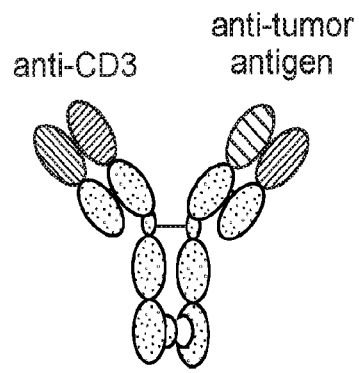
FIG. 2A-2E. Schematic models of bispecific human antibodies.
Figure 2B:
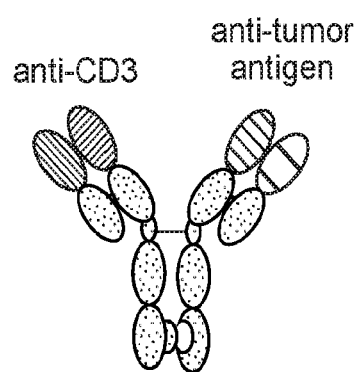
Figure 2C:
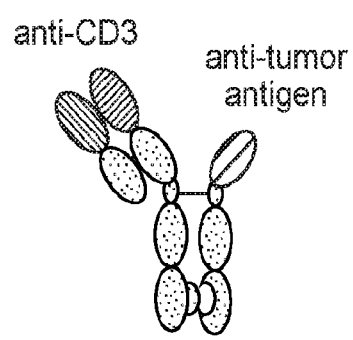
Figure 2D:
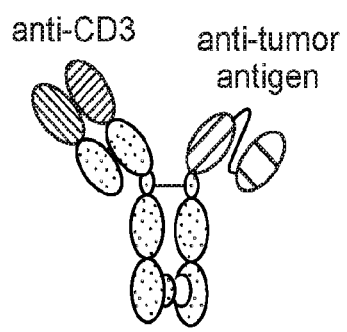
Figure 2E:
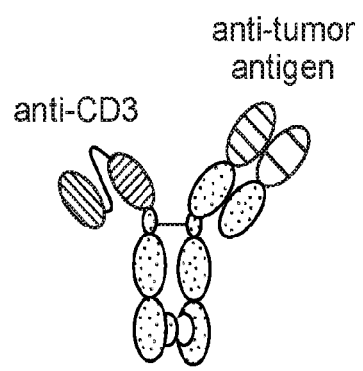

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias, including specifically B cell leukemias, T cell leukemias, etc. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

"Antibody-dependent cell-mediated cytotoxicity" and "ADCC" refer to a cell-mediated reaction in which nonspecific cytotoxic cells that express Fc receptors, such as natural killer cells, neutrophils, and macrophages, recognize bound antibody on a target cell and cause lysis of the target cell. ADCC activity may be assessed using methods, such as those described in U.S. Pat. No. 5,821,337. ADCP refers to antibody dependent cell-mediated phagocytosis.

"Effector cells" are leukocytes which express one or more constant region receptors and perform effector functions.

A "cytokine" is a protein released by one cell to act on another cell as an intercellular mediator. Cytokines of interest include, without limitation, cytokines released from activated T cells, for example IL-2, IFNγ, etc.

"Non-immunogenic" refers to a material that does not initiate, provoke or enhance an immune response where the immune response includes the adaptive and/or innate immune responses.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Homology" between two sequences is determined by sequence identity. If two sequences, which are to be compared with each other, differ in length, sequence identity preferably relates to the percentage of the nucleotide residues of the shorter sequence which are identical with the nucleotide residues of the longer sequence. Sequence identity can be determined conventionally with the use of computer programs such as the BESTFIT program (Wisconsin Sequence Analysis Package, Version 8 for UNIX, Genetics Computer Group, University Research Park, 575 Science Drive Madison, Wis. 53711). BESTFIT utilizes the local homology algorithm of Smith and Waterman, Advances in Applied Mathematics 2 (1981), 482-489, in order to find the segment having the highest sequence identity between two sequences. When using BESTFIT or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using BESTFIT, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Binding affinity" generally refers to the strength of the sum total of noncovalent interactions between a single binding site of a molecule (e.g., an antibody or other binding molecule) and its binding partner (e.g., an antigen or receptor). The affinity of a molecule X for its partner Y can generally be represented by the dissociation constant (Kd). Affinity can be measured by common methods known in the art, including those described herein. Low-affinity antibodies bind antigen (or receptor) weakly and tend to dissociate readily, whereas high-affinity antibodies bind antigen (or receptor) more tightly and remain bound longer.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Antibodies, also referred to as immunoglobulins, conventionally comprise at least one heavy chain and one light, where the amino terminal domain of the heavy and light chains is variable in sequence, hence is commonly referred to as a variable region domain, or a variable heavy (VH) or variable light (VH) domain. The two domains conventionally associate to form a specific binding region, although as well be discussed here, specific binding can also be obtained with heavy chain only variable sequences, and a variety of non-natural configurations of antibodies are known and used in the art.

A "functional" or "biologically active" antibody or antigen-binding molecule (including heavy chain only antibodies and bispecific three-chain antibody-like molecules (TCAs) herein) is one capable of exerting one or more of its natural activities in structural, regulatory, biochemical or biophysical events. For example, a functional antibody or other binding molecule, e.g. TCA, may have the ability to specifically bind an antigen and the binding may in turn elicit or alter a cellular or molecular event such as signaling transduction or enzymatic activity. A functional antibody or other binding molecule, e.g. TCA, may also block ligand activation of a receptor or act as an agonist or antagonist. The capability of an antibody or other binding molecule, e.g. TCA, to exert one or more of its natural activities depends on several factors, including proper folding and assembly of the polypeptide chains.

The term "antibody" herein is used in the broadest sense and specifically covers monoclonal antibodies, polyclonal antibodies, monomers, dimers, multimers, multispecific antibodies (e.g., bispecific antibodies), heavy chain only antibodies, three chain antibodies, single chain Fv, nanobodies, etc., and also include antibody fragments, so long as they exhibit the desired biological activity (Miller et al (2003) Jour. of Immunology 170:4854-4861). Antibodies may be murine, human, humanized, chimeric, or derived from other species.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. The immunoglobulins can be derived from any species. In one aspect, the immunoglobulin is of largely human origin.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region may comprise amino acid residues from a "complementarity determining region" or "CDR", and/or those residues from a "hypervariable loop". "Framework Region" or "FR" residues are those variable domain residues other than the hypervariable region residues as herein defined.

Variable regions of interest include at least one CDR sequence from the family 2 variable regions provided herein, usually at least 2 CDR sequences, and more usually 3 CDR sequences. Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342:877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlan et al. "Identification of specificity-determining residues in antibodies." Faseb J. 1995; 9:133-139., each of which is herein specifically incorporated by reference.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310). The light chains of antibodies from any vertebrate species can be assigned to one of two types, called κ and λ, based on the amino acid sequences of their constant domains.

A "functional Fc region" possesses an "effector function" of a native-sequence Fc region. Exemplary effector functions include C1q binding; CDC; Fc-receptor binding; ADCC; ADCP; down-regulation of cell-surface receptors (e.g., B-cell receptor), etc. Such effector functions generally require the Fc region to be interact with a receptor, e.g. the FcγRI; FcγRIIA; FcγRIIB1; FcγRIIB2; FcγRIIIA; FcγRIIIB receptors, and the law affinity FcRn receptor; and can be assessed using various assays as disclosed, for example, in definitions herein. A "dead" Fc is one that has been mutagenized to retain activity with respect to, for example, prolonging serum half-life, but which does not activate a high affinity Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce FcγRI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 of IgG2 residues at positions 233-236 and IgG4 residues at positions 327, 330 and 331 greatly reduces ADCC and CDC (see, for example, Armour K L. et al., 1999 Eur J Immunol. 29(8): 2613-24; and Shields R L. et al., 2001. J Biol Chem. 276(9):6591-604). Other Fc variants are possible, including without limitation one in which a region capable of forming a disulfide bond is deleted, or in which certain amino acid residues are eliminated at the N-terminal end of a native Fc form or a methionine residue is added thereto. Thus, in one embodiment of the invention, one or more Fc portions of the scFc molecule can comprise one or more mutations in the hinge region to eliminate disulfide bonding. In yet another embodiment, the hinge region of an Fc can be removed entirely. In still another embodiment, the molecule can comprise an Fc variant.

Further, an Fc variant can be constructed to remove or substantially reduce effector functions by substituting, deleting or adding amino acid residues to effect complement binding or Fc receptor binding. For example, and not limitation, a deletion may occur in a complement-binding site, such as a C1q-binding site. Techniques of preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

The Fc may be in the form of having native sugar chains, increased sugar chains compared to a native form or decreased sugar chains compared to the native form, or may be in an aglycosylated or deglycosylated form. The increase, decrease, removal or other modification of the sugar chains may be achieved by methods common in the art, such as a chemical method, an enzymatic method or by expressing it in a genetically engineered production cell line. Such cell lines can include microorganisms, e.g. Pichia Pastoris, and mammalians cell line, e.g. CHO cells, that naturally express glycosylating enzymes. Further, microorganisms or cells can be engineered to express glycosylating enzymes, or can be rendered unable to express glycosylation enzymes (See e.g., Hamilton, et al., Science, 313:1441 (2006); Kanda, et al, J. Biotechnology, 130:300 (2007); Kitagawa, et al., J. Biol. Chem., 269 (27): 17872 (1994); Ujita-Lee et al., J. Biol. Chem., 264 (23): 13848 (1989); Imai-Nishiya, et al, BMC Biotechnology 7:84 (2007); and WO 07/055916). As one example of a cell engineered to have altered sialylation activity, the alpha-2,6-sialyltransferase 1 gene has been engineered into Chinese Hamster Ovary cells and into sf9 cells. Antibodies expressed by these engineered cells are thus sialylated by the exogenous gene product. A further method for obtaining Fc molecules having a modified amount of sugar residues compared to a plurality of native molecules includes separating said plurality of molecules into glycosylated and non-glycosylated fractions, for example, using lectin affinity chromatography (See e.g., WO 07/117505). The presence of particular glycosylation moieties has been shown to alter the function of Immunoglobulins. For example, the removal of sugar chains from an Fc molecule results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. Additional important modifications include sialylation and fucosylation: the presence of sialic acid in IgG has been correlated with anti-inflammatory activity (See e.g., Kaneko, et al, Science 313:760 (2006)), whereas removal of fucose from the IgG leads to enhanced ADCC activity (See e.g., Shoj-Hosaka, et al, J. Biochem., 140:777 (2006)).

In alternative embodiments, antibodies of the invention may have an Fc sequence with enhanced effector functions, e.g. by increasing their binding capacities to FcγRIIIA and increasing ADCC activity. For example, fucose attached to the N-linked glycan at Asn-297 of Fc sterically hinders the interaction of Fc with FcγRIIIA, and removal of fucose by glyco-engineering can increase the binding to FcγRIIIA, which translates into >50-fold higher ADCC activity compared with wild type IgG1 controls. Protein engineering, through amino acid mutations in the Fc portion of IgG1, has generated multiple variants that increase the affinity of Fc binding to FcγRIIIA. Notably, the triple alanine mutant S298A/E333A/K334A displays 2-fold increase binding to FcγRIIIA and ADCC function. S239D/I332E (2X) and S239D/I332E/A330L (3X) variants have a significant increase in binding affinity to FcγRIIIA and augmentation of ADCC capacity in vitro and in vivo. Other Fc variants identified by yeast display also showed the improved binding to FcγRIIIA and enhanced tumor cell killing in mouse xenograft models. See, for example Liu et al. (2014) JBC 289(6):3571-90, herein specifically incorporated by reference.

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, an antibody having an Fc region according to this invention can comprise an antibody with or without K447.

"Fv" is the minimum antibody fragment, which contains a complete antigen-recognition and antigen-binding site. The CD3 binding antibodies of the invention comprise a dimer of one heavy chain and one light chain variable domain in tight, non-covalent association; however additional antibodies, e.g. for use in a multi-specific configuration, may comprise a VH in the absence of a VL sequence. Even a single variable domain (or half of an Fv comprising only three hypervariable regions specific for an antigen) has the ability to recognize and bind antigen, although the affinity may be lower than that of two domain binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Humanized" forms of non-human (e.g., rodent) antibodies, including single chain antibodies, are chimeric antibodies (including single chain antibodies) that contain minimal sequence derived from non-human immunoglobulin. See, for example, Jones et al, (1986) Nature 321:522-525; Chothia et al (1989) Nature 342:877; Riechmann et al (1992) J. Mol. Biol. 224, 487-499; Foote and Winter, (1992) J. Mol. Biol. 224:487-499; Presta et al (1993) J. Immunol. 151, 2623-2632; Werther et al (1996) J. Immunol. Methods 157:4986-4995; and Presta et al (2001) Thromb. Haemost. 85:379-389. For further details, see U.S. Pat. Nos. 5,225, 539; 6,548,640; 6,982,321; 5,585,089; 5,693,761; 6,407, 213; Jones et al (1986) Nature, 321:522-525; and Riechmann et al (1988) Nature 332:323-329.

The term "single chain antibody" as used herein means a single polypeptide chain containing one or more antigen binding domains that bind an epitope of an antigen, where such domains are derived from or have sequence identity with the variable region of an antibody heavy or light chain. Parts of such variable region may be encoded by $V_H$ or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments. V-, D- and J-gene segments may be derived from humans and various animals including birds, fish, sharks, mammals, rodents, non-human primates, camels, lamas, rabbits and the like.

The CD3-binding antibodies of the invention find particular utility in multi-specific configurations, which include without limitation bispecific antibodies, trifunctional antibodies, etc. A large variety of methods and protein configurations are known and use in bispecific monoclonal antibodies (BsMAB), tri-specific antibodies, etc.

First-generation BsMAbs consisted of two heavy and two light chains, one each from two different antibodies. The two Fab regions are directed against two antigens. The Fc region is made up from the two heavy chains and forms the third binding site with the Fc receptor on immune cells (see for example Lindhofer et al., The Journal of Immunology, Vol 155, p 219-225, 1995). The antibodies may be from the same or different species. For example, cell lines expressing rat and mouse antibodies secrete functional bispecific Ab because of preferential species-restricted heavy and light chain pairing. In other embodiments the Fc regions are designed to only fit together in specific ways.

Other types of bispecific antibodies include chemically linked Fabs, consisting only of the Fab regions. Two chemically linked Fab or Fab2 fragments form an artificial antibody that binds to two different antigens, making it a type of bispecific antibody. Antigen-binding fragments (Fab or Fab2) of two different monoclonal antibodies are produced and linked by chemical means like a thioether (see Glennie, M J et al., Journal of immunology 139, p 2367-75, 1987; Peter Borchmann et al., Blood, Vol. 100, No. 9, p 3101-3107, 2002).

Various other methods for the production of multivalent artificial antibodies have been developed by recombinantly fusing variable domains of two antibodies. A single-chain variable fragment (scFv) is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. Bispecific single-chain variable fragments (di-scFvs, bi-scFvs) can be engineered by linking two scFvs with different specificities. A single peptide chain with two VH and two VL regions is produced, yielding bivalent scFvs.

Bispecific tandem scFvs are also known as bi-specific T-cell engagers (BiTEs). Bispecific scFvs can be created with linker peptides that are too short for the two variable regions to fold together (about five amino acids), forcing scFvs to dimerize. This type is known as diabodies (Adams et al., British journal of cancer 77, p 1405-12, 1998). The Dual-Affinity Re-Targeting (DART) platform technology (MACROGENICS, Rockville, Md.). This fusion protein technology uses two single-chain variable fragments (scFvs) of different antibodies on a single peptide chain of about 55 kilodaltons. SCORPION Therapeutics (EMERGENT BIO-SOLUTIONS, INC., Seattle, Wash.) combines two antigen-binding domains in a single chain protein. One binding domain is on the C-terminus and a second binding domain on the N-terminus of an effector domain, based on immunoglobulin Fc regions.

Tetravalent and bispecific antibody-like proteins also include DVD-Igs which are engineered from two monoclonal antibodies (Wu, C. et al., Nature Biotechnology, 25, p 1290-1297, 2007). To construct the DVD-Ig molecule, the V domains of the two mAbs are fused in tandem by a short linker (TVAAP, SEQ ID NO:27) with the variable domain of the first antibody light (VL) chain at the N terminus, followed by the other antibodies VL and Ck to form the DVD-Ig protein light chain. Similarly, the variable regions of the heavy (VH) chain of the two mAbs are fused in tandem by a short linker (ASTKGP, SEQ ID NO:28) with the first antibody at the N terminus, followed by the other antibody and the heavy chain constant domains to form the DVD-Ig protein heavy chain (VH1/VL1). All light chain and heavy chain constant domains are preserved in the DVD-Ig design, as they are critical for the formation of a disulfide-linked full IgG-like molecule. Cotransfection of mammalian cells with expression vectors encoding the DVD-Ig light chain and heavy chain leads to the secretion of a single species of an IgG-like molecule with molecular weight of approximately 200 kDa. This molecule has now four binding sites, 2 from each mAb.

The term "bispecific three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments.

A TCA protein makes use of a heavy chain only antibody" or "heavy chain antibody" or "heavy chain polypeptide" as used herein means a single chain antibody comprising heavy chain constant regions CH2 and/or CH3 and/or CH4 but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment the heavy chain is composed of an antigen binding domain, and at least one CH (CH1, CH2, CH3, or CH4) domain but no hinge region. The heavy chain only antibody can be in the form of a dimer, in which two heavy chains are disulfide bonded other otherwise, covalently or non-covalently attached with each other. The heavy chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular IgG1 subtype.

Heavy chain antibodies constitute about one fourth of the IgG antibodies produced by the camelids, e.g. camels and llamas (Hamers-Casterman C., et al. Nature. 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. J. Biol. Chem. 276, 26285-26290 (2001)). Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)). Sharks have also been shown to have a single VH-like domain in their antibodies termed VNAR. (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

An antibody or antigen-binding molecule, including the heavy chain only antibodies and bispecific three-chain antibody-like molecules (TCAs) herein, "which binds" an antigen of interest, is one that binds the antigen with sufficient affinity such that the antibody or binding molecule is useful as a diagnostic and/or therapeutic agent in targeting the antigen, and does not significantly cross-react with other proteins. In such embodiments, the extent of binding of the antibody or other binding molecule to a non-targeted antigen will be no more than 10% as determined by fluorescence activated cell sorting (FACS) analysis or radioimmunoprecipitation (RIA).

Proteins

The present invention provides a family of closely related antibodies that bind to and activate signaling through CD3, e.g. activation of $CD3^+$ T cells. The antibodies within the family comprise a set of CDR sequences as defined herein, and are exemplified by the provided VH sequences of SEQ ID NO:1-18. The family of antibodies provides a number of benefits that contribute to utility as clinically therapeutic agent(s). The antibodies within the family include members with a range of binding affinities, allowing the selection of a specific sequence with a desired affinity. The ability to fine tune affinity is of particular importance to manage the level of CD3 activation in an individual being treated, and thereby reduce toxicity. For example, if low abundant tumor antigens (less than 10,000 molecules per cell) are targeted, it is anticipated that high affinity CD3 binders (<30 nM) are preferred. If highly abundant tumor antigens (more than 50,000 molecules per cell) are targeted, CD3 binders with low affinities (>50 nM) are preferred. Separately evaluated from affinity can be the propensity of the antibody to induce release of cytokines when bound to a T cell, e.g. release of IL-2, IFNγ, etc., where reduced cytokine release may be desirable.

A suitable antibody may be selected from those provided herein for development and use, including without limitation use as a bispecific antibody. Determination of affinity for a candidate protein can be performed using methods known in the art, e.g. BIACORE measurements, etc. Members of the antibody family may have an affinity for CD3 with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for activation of T cells in, for example, and in vitro or pre-clinical model, and assessment of potential toxicity. Determination of cytokine release can be evaluated using any convenient method, including without limitation the assays described in the examples.

Engagement of the T cell receptor (TCR), either by binding MH-peptide complexes or anti-TCR/CD3 antibodies, initiates T cell activation. Examples of anti-TCR/CD3 antibodies that activate T cells are OKT3 and UCHT1. These anti-CD3 antibodies cross-compete for binding to CD3 on T cells and are routinely used in T cell activation assays. Anti-CD3 antibodies of this invention cross-compete with OKT3 for binding to human CD3. Depending on the binding affinity for CD3 and epitope on CD3, anti-CD3 antibodies activated T cells with different functional outcomes. In vitro incubation of human T cells with low affinity anti-CD3 antibodies resulted in incomplete activation of T cells, low IL-2 and IL-10 production. In contrast, high-affinity CD3 binders activated T cells to produce significantly more IL-2 and other cytokines. The low-affinity anti-CD3 antibodies are considered partial agonists that selectively induce some effector functions, potent tumor killing and CD69 upregulation, while failing to induce others, such as IL-2 and IL-10 production. The high-affinity binders of this invention are full-agonists activating many immune effector functions of T cells. The strength of the interaction with CD3 and the epitope recognized resulted in qualitatively different activation of T cells. Maximal cytokine production of T cells activated by low-affinity anti-CD3 antibodies was lower than maximal activation by high-affinity anti-CD3 antibodies. In some embodiments, an antibody of the invention results in a lower release of one or both of IL-2 and IL-10 when combined with T cells in an activation assay when compared to a reference anti-CD3 antibody in the same assay, where the reference antibody can be ID 304703 (SEQ ID NO:22) or an antibody of equivalent affinity. The maximal release of IL-2 and/or IL-10 can be less than about 75% of the release by the reference antibody, less than about 50% of the release by the reference antibody, less than about 25% of the release by the reference antibody, and may be less than about 10% of the release by a reference antibody.

In some embodiments of the invention, bispecific or multispecific antibodies are provided, which may have any of the configurations discussed herein, including without limitation a three chain bispecific. Bispecific antibodies comprise at least the heavy chain variable region of an antibody specific for a protein other than CD3, and may comprise a heavy and light chain variable region. In some such embodiments, the second antibody specificity binds to a tumor associated antigen, a targeting antigen, e.g. integrins, etc., a pathogen antigen, a checkpoint protein, and the like. Various formats of bispecific antibodies are within the ambit of the invention, including without limitation single chain polypeptides, two chain polypeptides, three chain polypeptides, four chain polypeptides, and multiples thereof.

The family of CD3 specific antibodies comprise a VH domain, comprising CDR1, CDR2 and CDR3 sequences in a human VH framework. The CDR sequences may be situated, as an example, in the region of around amino acid residues 26-33; 51-58; and 97-112 for CDR1, CDR2 and CDR3, respectively, of the provided exemplary variable region sequences set forth in SEQ ID NO:1-18. It will be understood by one of skill in the art that the CDR sequences may be in different position if a different framework sequence is selected, although generally the order of the sequences will remain the same.

The CDR sequences for a family 2 antibody may have the following sequence formulas. An X indicates a variable amino acid, which may be specific amino acids as indicated below.

CDR1
$G_1\ F_2\ T_3\ F_4\ X_5\ X_6\ Y_7\ A_8$ where:
$X_5$ may be any amino acid; in some embodiments $X_5$ is D, A or H; in some embodiments $X_5$ is D.
$X_6$ may be any amino acid; in some embodiments $X_6$ is D or N; in some embodiments $D_6$ is D.

In some embodiments a CDR1 sequence of a family 2 anti-CD3 antibody comprises the sequence set forth in any of SEQ ID NO:1-18, residues 26-33.

CDR2
$I_1,\ S_2,\ W_3,\ N_4,\ S_5,\ G_6,\ S_7,\ I_8,$

In some embodiments a CDR2 sequence of a family 2 anti-CD3 antibody comprises the sequence set forth in any of SEQ ID NO:1-18, residues 51-58.

CDR3
$A_{1''}\ K_{2''}\ D_{3''}\ S_{4''}\ R_{5''}\ G_{6''}\ Y_{7''}\ G_{8''}\ X_{9''}\ Y_{10''}\ X_{11''}\ X_{12''}$
$G_{13''}\ G_{12''}\ A_{15''}\ Y_{16''}$ where:
$X_{9''}$ may be any amino acid, in some embodiments $X_{9''}$ is D or S; in some embodiments $X_{9''}$ is D;
$X_{11''}$ may be any amino acid, in some embodiments $X_{11''}$ is R or S;
$X_{12''}$ may be any amino acid, in some embodiments $X_{12''}$ is L or R.

In some embodiments a CD3 sequence of a family 2 anti-CD3 antibody has the formula A K D S R G Y G D Y $X_{11''}\ X_{12''}$ G G A Y where $X_{11''}$ and $X_{12''}$ are as defined above. In some embodiments a CDR3 sequence of a family 2 anti-CD3 antibody comprises the sequence set forth in any of SEQ ID NO:1-18, residues 97-112.

In some embodiments the CD3-binding VH domain is paired with a light chain variable region domain. In some such embodiments the light chain is a fixed light chain. In some embodiments the light chain comprises a VL domain with CDR1, CDR2 and CDR3 sequences in a human VL framework. The CDR sequences may be those of SEQ ID NO:19. In some embodiments, the CDR1 sequence comprises amino acid residues 27-32; 50-52; 89-97 for CDR1, CDR2, CDR3, respectively.

In some embodiments the CDR sequences of a family 2 antibody have a sequence with at least 85% identity, at least 90% identity, at least 95% identity, at least 99% identity relative to a CDR sequence or set of CDR sequences in any one of SEQ ID NO:1-18. In some embodiments a CDR sequence of the invention comprises one, two, three or more amino acid substitutions relative to a CDR sequence or set of CDR sequences in any one of SEQ ID NO:1-18. In some embodiments said amino acid substitution(s) are one or more of position 5 or 10 of CDR1, position 2, 6 or 7 of CDR2, position 1, 8, 9 or 10 of CDR3, relative to the formulas provided above.

Where a protein of the invention is a bispecific antibody, one binding moiety, i.e. VH/VL combination or VH only, is specific for human CD3 while the other arm may be specific for target cells, including cancer cells, such as cells of ovarian, breast, gastrointestinal, brain, head and neck, prostate, colon, and lung cancers, and the like, as well as hematologic tumors such as B-cell tumors, including leukemias, lymphomas, sarcomas, carcinomas, neural cell tumors, squamous cell carcinomas, germ cell tumors, metastases, undifferentiated tumors, seminomas, melanomas, myelomas, neuroblastomas, mixed cell tumors, neoplasias caused by infectious agents, and other malignancies, cells infected with a pathogen, autoreactive cells causing inflammation and/or autoimmunity. The non-CD3 moiety can also be specific for an immune regulatory protein, as will be described herein.

Tumor-associated antigens (TAAs) are relatively restricted to tumor cells, whereas tumor-specific antigens (TSAs) are unique to tumor cells. TSAs and TAAs typically are portions of intracellular molecules expressed on the cell surface as part of the major histocompatibility complex.

Tissue specific differentiation antigens are molecules present on tumor cells and their normal cell counterparts. Tumor-associated antigens known to be recognized by therapeutic mAbs fall into several different categories. Hematopoietic differentiation antigens are glycoproteins that are usually associated with cluster of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA, epidermal growth factor receptor (EGFR; also known as ERBB1)' ERBB2 (also known as HER2), ERBB3, MET (also known as HGFR), insulin-like growth factor 1 receptor (IGF1R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11). Antigens involved in angiogenesis are usually proteins or growth factors that support the formation of new microvasculature, including vascular endothelial growth factor (VEGF), VEGF receptor (VEGFR), integrin αVβ3 and integrin α5β1. Tumor stroma and the extracellular matrix are indispensable support structures for a tumor. Stromal and extracellular matrix antigens that are therapeutic targets include fibroblast activation protein (FAP) and tenascin.

Examples of therapeutic antibodies useful in bispecific configurations include, without limitation, rituximab; Ibritumomab; tiuxetan; tositumomab; Brentuximab; vedotin; Gemtuzumab; ozogamicin; Alemtuzumab; IGN101; adecatumumab; Labetuzumab; huA33; Pemtumomab; oregovomab; CC49 (minretumomab); cG250; J591; MOv18; MORAb-003 (farletuzumab); 3F8, ch14.18; KW-2871; hu3S193; IgN311; Bevacizumab; IM-2C6; CDP791; Etaracizumab; Volociximab; Cetuximab, panitumumab, nimotuzumab; 806; Trastuzumab; pertuzumab; MM-121; AMG 102, METMAB; SCH 900105; AVE1642, IMC-A12, MK-0646, R1507; CP 751871; KB004; IIIA4; Matapumumab (HGS-ETR1); HGS-ETR2; CS-1008; Denosumab; Sibrotuzumab; F19; and 8106.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD1 are PD1 ligand 1 (PDL1; also known as B7-H1 and CD274) and PDL2 (also known as B7-DC and CD273). PDL1 is expressed on cancer cells and through binding to its receptor PD1 on T cells it inhibits T cell activation/function.

Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR) and the family of killer inhibitory receptors have each been associated with the inhibition of lymphocyte activity and in some cases the induction of lymphocyte anergy. Antibody targeting of these receptors can be used in the methods of the invention.

Agents that agonize an immune costimulatory molecule are also useful in the methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages.

Anti CCR4 (CD194) antibodies of interest include humanized monoclonal antibodies directed against C-C chemokine receptor 4 (CCR4) with potential anti-inflammatory and antineoplastic activities. CCR2 is expressed on inflammatory macrophages that can be found in various inflammatory conditions, e.g. rheumatoid arthritis; and have also been identified as expressed on tumor promoting macrophages. CCR2 is also expressed on regulatory T cells, and the CCR2 ligand, CCL2, mediates recruitment of regulatory T cells into tumors. Regulatory T cells suppress a response for anti-tumor T cells and thus their inhibition or depletion is desired.

Producing Proteins of the Invention

Although antibodies can be prepared by chemical synthesis, they are typically produced by methods of recombinant DNA technology, such as co-expression of all the chains making up the protein in a single recombinant host cell, or co-expression of a heavy chain polypeptide and an antibody, e.g. a human antibody. In addition, the antibody heavy and light chains can also be expressed using a single polycistronic expression vector. Purification of individual polypeptides is achieved using standard protein purification technologies such as affinity (protein A) chromatography, size exclusion chromatography and/or hydrophobic interaction chromatography. Bispecifics are sufficiently different in size and hydrophobicity that purification can be performed using standard procedures.

The amount of antibody and heavy chain polypeptide produced in a single host cell can be minimized through engineering of constant regions of the antibody and the heavy chain such that homodimerization is favored over heterodimerization, e.g. by introducing self-complementary interactions (see e.g. WO 98/50431 for possibilities, such as "protuberance-into-cavity" strategies (see WO 96/27011)). It is therefore another aspect of the present invention to provide a method for producing a bispecific in a recombinant host, the method including the step of: expressing in a recombinant host cell a nucleic acid sequences encoding at least two heavy chain polypeptides, wherein said heavy chain polypeptides differ in their constant regions sufficiently to reduce or prevent homodimer formation but increase bispecific formation.

Where the protein comprises three chains, e.g. FlicAbs™, they may be produced by co-expression of the three chains (2 heavy chains and one light chain) making up the molecule in a single recombinant host cell.

For recombinant production of the proteins herein, one or more nucleic acids encoding all chains, e.g. 2, 3 4, etc. are isolated and inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

In a preferred embodiment, the host cell according to the method of the invention is capable of high-level expression of human immunoglobulin, i.e. at least 1 pg/cell/day, preferably at least 10 pg/cell/day and even more preferably at least 20 pg/cell/day or more without the need for amplification of the nucleic acid molecules encoding the single chains in said host cell.

Pharmaceutical Composition

It is another aspect of the present invention to provide pharmaceutical compositions comprising one or more proteins of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

Therapeutic formulations of the proteins used in accordance with the present invention are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Anti-CD3 antibody formulations are disclosed, for example, in U.S. Patent Publication No. 20070065437, the entire disclosure is expressly incorporated by reference herein. Similar formulations can be used for the proteins of the present invention. The main components of such formulations are a pH buffering agent effective in the range of 3.0 to 6.2, a salt, a surfactant, and an effective amount of a bispecific with anti-CD3 specificity.

Methods of Use

Methods are provided for treating or reducing disease, including without limitation infection, autoimmune disease, primary or metastatic cancer, etc. in a regimen comprising contacting the targeted cells with an antigen-binding composition of the invention, particularly where the antigen-binding composition is a multi-specific antibody suitable for the condition being treated, e.g. where one binding moiety specifically binds to a tumor associated antigen for treatment of the relevant cancer cells; a binding moiety specific for a pathogen of interest for treatment of the relevant infection, and the like. Such methods include administering to a subject in need of treatment a therapeutically effective amount or an effective dose of the agents of the invention, including without limitation combinations of the reagent with a chemotherapeutic drug, radiation therapy, or surgery.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subjects response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, hematologic cancers such as leukemias and lymphomas, melanomas, sarcomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions for the treatment of disease can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

The invention now being fully described, it will be apparent to one of ordinary skill in the art that various changes and modifications can be made without departing from the spirit or scope of the invention.

EXAMPLES

Example 1 Genetically Engineered Rats Expressing Heavy Chain-Only Antibodies A human IgH locus was constructed and assembled in several parts, which involved the modification and joining of rat C region genes, which were then joined downstream of human $V_H6$-D-$J_H$ region. Two BACs with separate clusters of human $V_H$ genes were then co-injected with a BAC encoding the assembled (human $V_H6$-D-$J_H$-rat C) fragment.

Transgenic rats carrying artificial heavy chain immunoglobulin loci in unrearranged configuration were generated. The included constant region genes encode IgM, IgD, IgG2b, IgE, IgA and 3' enhancer. RT-PCR and serum analysis (ELISA) of transgenic rats revealed productive rearrangement of transgenic immunoglobulin loci and expression of heavy chain only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes. Immunization of transgenic rats resulted in production of high titer serum responses of antigen-specific heavy chain antibodies. These transgenic rats expressing heavy chain antibodies with a human VDJ region were called UniRats®.

Example 2 Genetically Engineered Rats Expressing Fixed Light Chain Antibodies

Transgenic human antibody repertoires were generated from H-chains with diverse $(V_H\text{-}D\text{-}J_H)_n$ rearrangement in combination with a unique L-chain. For this a rearranged L-chain, human Vk-Jk1-Ck, was integrated in the rat germline by DNA microinjection and the obtained transgenic animals were bred with a previously described rat strain that expresses a human H-chain repertoire naturally (Osborn et al., 2013). This new rat strain was named OmniFlic®.

Immunizations of OmniFlic® rats, using many different antigens, produced high levels of antigen-specific IgG similar to other transgenic rats carrying the same IgH locus. Repertoire analysis by RT-PCR identified highly variable VH-gene rearrangements at high transcript and protein levels. In addition, only one L-chain product, also expressed at high level, was identified.

Antigen-specific binders from OmniFlic® were obtained by NGS and selection from cDNA libraries (yeast, E. coli, phage), which upon sequencing identified diverse H-chain transcripts. For the expression in mammalian cells hypermutated H-chain constructs were transfected in combination with the original transgenic Igk sequence. In this rearranged Vk-Jk1-Ck no mutational changes were allowed and always the same L-chain was expressed with various H-chain products to generate monoclonal human IgG.

Example 3 Generation of Antigen-Specific Antibodies in Transgenic Rats

For the generation of antigen-specific heavy chain antibodies in rats, genetically engineered rats expressing were immunized in two ways.

Immunization with recombinant extracellular domains of PD-L1 and BCMA. Recombinant extracellular domains of PD-L1 and BCMA were purchased from R&D Systems and were diluted with sterile saline and combined with adjuvant. Immunogens were either combined with Complete Freund's Adjuvant (CFA) and Incomplete Freund's Adjuvant (IFA) or Titermax® and Ribi adjuvants. The first immunization (priming) with immunogen in CFA or Titermax® was administered in the left and right legs. After the first immunization with immunogens in CFA two more immunizations in IFA (boosters) or 4 more immunizations in Ribi and one more in Titermax® were administered in each leg. This sequence of immunizations leads to the development of B cells producing high affinity antibodies. The immunogen concentrations were 10 microgram per leg. Serum was collected from rats at the final bleed to determine serum titers.

For the generation of anti-human CD388 antibodies genetically engineered rats were immunized using DNA-based immunization protocols.

OmniFlic® rats were immunized with human and cynomolgus CD3-epsilon/delta constructs at ALDEVRON, Inc. (Fargo, N. Dak.) using the GENOVAC Antibody Technology. Draining lymph nodes were harvested after the final boost and RNA isolated. Following cDNA synthesis, the IgH heavy chain antibody repertoire was characterized by Next Generation Sequencing and our proprietary in-house software. Candidate antigen-specific VH sequences showing evidence of antigen-specific positive selection were selected. Several hundred VH sequences encoding FlicAbs™ were selected for gene assembly and cloned into an expression vector. Subsequently, fully human FlicAb™ IgG1 antibodies were expressed in HEK cells for analysis by Flow and ELISA. Human FlicAbs™ were tested for binding to primary human T cells and Jurkat cells by flow. In addition, human FlicAbs™ were tested using recombinant $CD3\delta_\epsilon$ proteins in ELISA. All FlicAbs™ with positive binding for human T cells are listed in FIGS. 1 and 2. Selected sequences were further characterized in T cell activation assays.

Example 4 Characterization of Antibodies

The data table of FIG. 3 summarizes the behavior of anti-CD3 antibodies of family 2 in monospecific and bispecific format. Column 1 shows the sequence ID for the anti-CD3 VH sequence. Column 2 shows the MFI value for Jurkat cell binding of the parental monospecific anti-CD3. Column 3 shows the MFI value for cyno T-cell binding of the parental monospecific anti-CD3. Column 4 shows the name of the aCD3:aBCMA bispecific antibody. Column 5 shows the picograms of IL-2 released by pan T-cells stimulated by the bispecific antibody binding the BCMA protein coated on plastic at the dose indicated. Column 6 shows the picograms of IL-6 released by pan T-cells stimulated by the bispecific antibody binding the BCMA protein coated on plastic at the dose indicated. Column 7 shows the picograms of IL-10 released by pan T-cells stimulated by the bispecific antibody binding the BCMA protein coated on plastic at the dose indicated. Column 8 shows the picograms of IFN-γ released by pan T-cells stimulated by the bispecific antibody binding the BCMA protein coated on plastic at the dose indicated. Column 9 shows the picograms of TNFα released by pan T-cells stimulated by the bispecific antibody binding the BCMA protein coated on plastic at the dose indicated. Column 10 shows the $EC_{50}$ of bispecific antibody-mediated U266 tumor cell lysis in presence of human pan T-cells. Column 11 shows the percent lysis of U266 tumor cells in the presence of bispecific antibody and human pan T-cells at a dose of 333 ng/mL of bispecific antibody. Column 12 shows the protein binding affinity of the anti-CD3 arm of the bispecific antibody measured by Octet®. Column 13 shows the MFI value for Jurkat cell binding of the bispecific antibody.

Example 5 Bispecific Antibody Characterization

Figure 4:
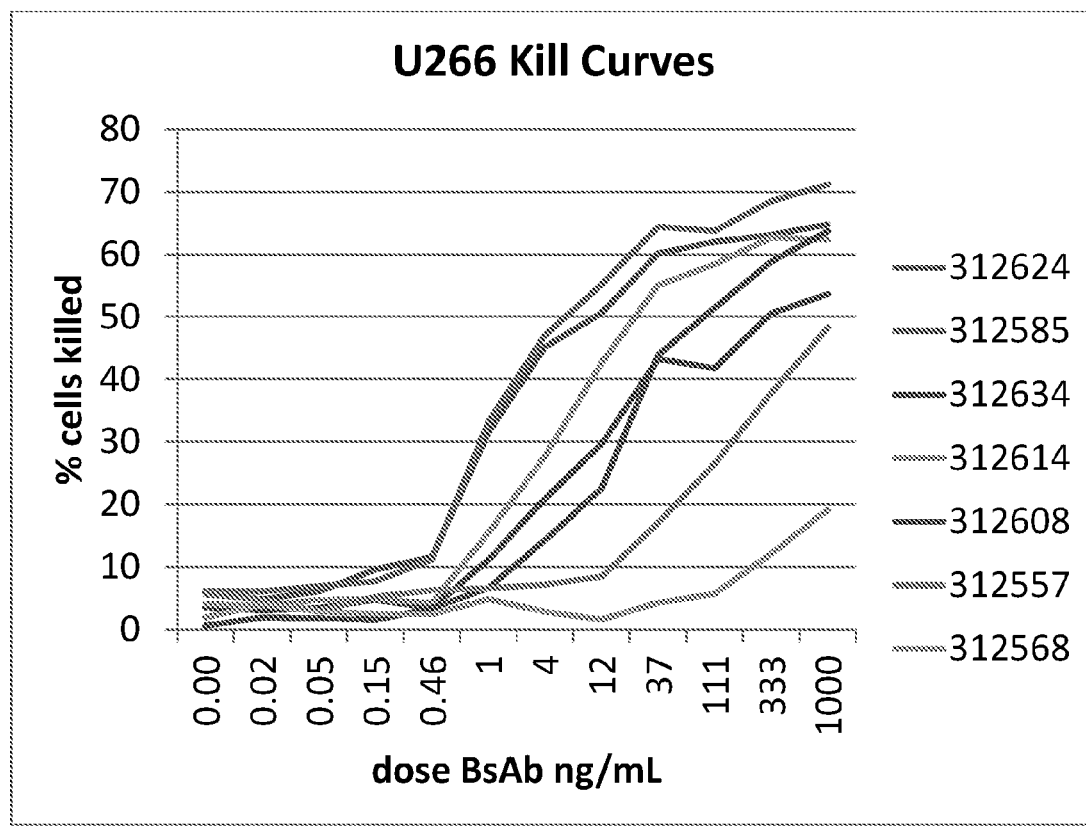
FIG. 4. Bispecific antibody-mediated tumor cell lysis. Seven αCD3_fam2:aBCMA bispecific antibodies, each with a unique anti-CD3 arm and a common anti-BCMA arm, were tested for the ability to kill U266 BCMA+ tumor cells through redirection of activated primary T cells. In this experiment U266 cells that express BCMA were mixed with activated pan T-cells in a 10:1 E:T ratio along with the addition of bispecific antibody. The x-axis shows the concentration of antibody used and the y-axis shows the % lysis of tumor cells 6 hours after addition of antibody.

Seven αCD3_fam2:aBCMA bispecific antibodies, each with a unique anti-CD3 arm and a common anti-BCMA arm, were tested for the ability to kill U266 BCMA+ tumor cells through redirection of activated primary T cells. In this experiment U266 cells that express BCMA were mixed with activated pan T-cells in a 10:1 E:T ratio along with the addition of bispecific antibody. Shown in FIG. 4, the x-axis shows the concentration of antibody used and the y-axis shows the % lysis of tumor cells 6 hours after addition of antibody.

Figure 5:
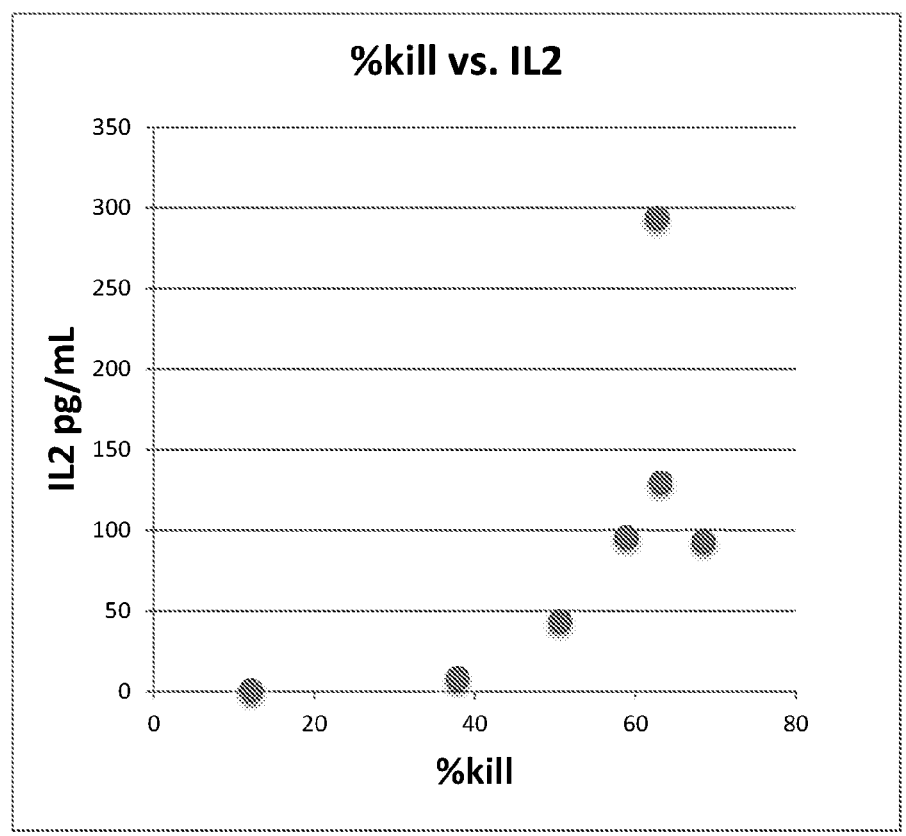
FIG. 5. Bispecific U266 killing activity correlated with IL-2 release. A comparison of bispecific antibody-mediated tumor cell lysis activity with IL-2 cytokine release is shown in the scatter plot. The correlation between IL-2 production and U266 tumor cell lysis is $R^2$=0.37.
Figure 6:
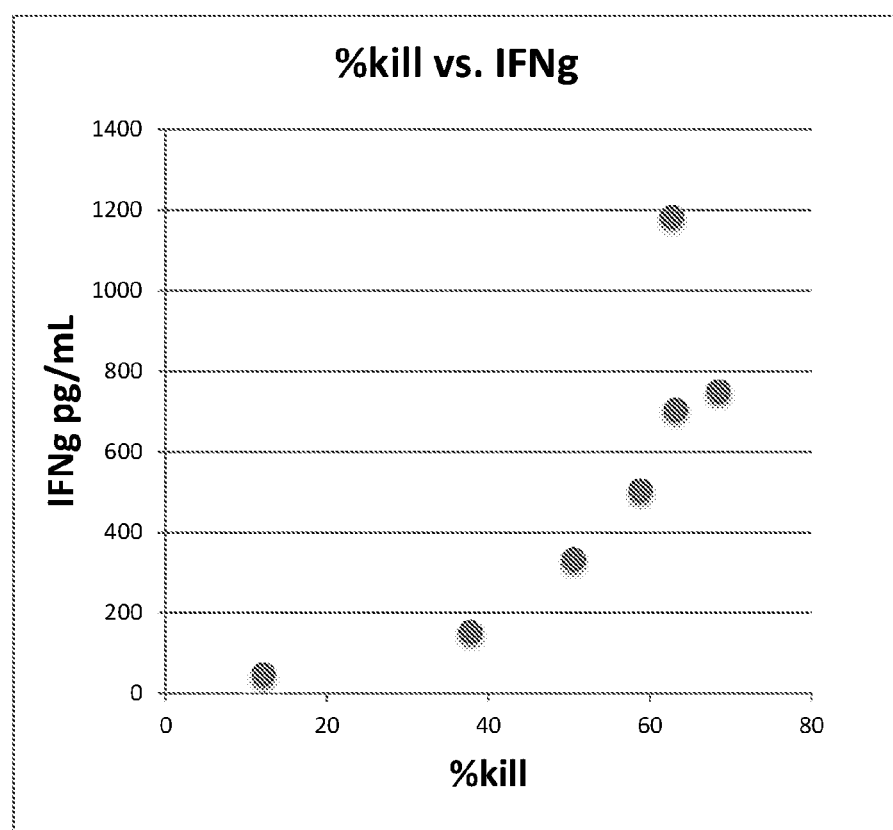
FIG. 6. Bispecific U266 killing activity correlated with IFN-γ release. A comparison of bispecific antibody-mediated tumor cell lysis activity with IFN-γ cytokine release is shown in the scatter plot. The correlation between IFN-g production and U266 tumor cell lysis is $R^2$=0.53.
Figure 7:
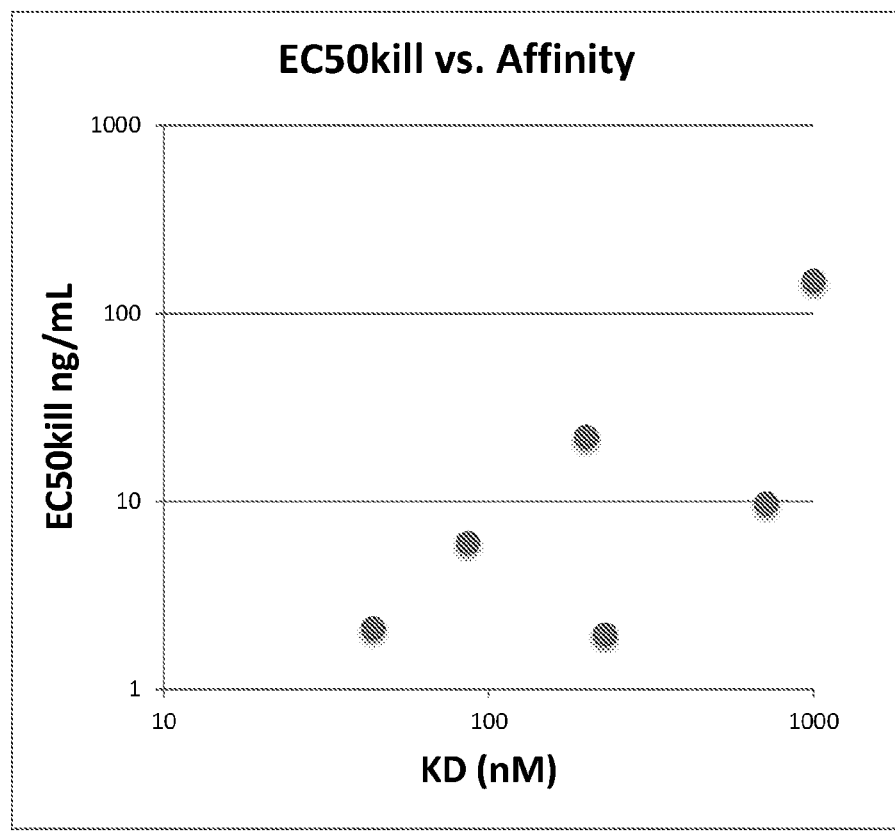
FIG. 7. Bispecific U266 killing activity correlated with anti-CD3 binding affinity. A comparison of bispecific antibody-mediated U266 tumor cell lysis activity with anti-CD3 binding affinity is shown in the scatter plot. The correlation between U266 killing EC50 and protein binding affinity is $R^2$=0.93.

A comparison of bispecific antibody-mediated tumor cell lysis activity with IL-2 cytokine release is shown in the scatter plot of FIG. 5. The correlation between IL-2 production and U266 tumor cell lysis is $R^2$=0.37. A comparison of bispecific antibody-mediated tumor cell lysis activity with IFN-γ cytokine release is shown in the scatter plot of FIG. 6. The correlation between IFN-γ production and U266 tumor cell lysis is $R^2=0.53$. A comparison of bispecific antibody-mediated U266 tumor cell lysis activity with anti-CD3 binding affinity is shown in the scatter plot of FIG. 7. The correlation between U266 killing $EC_{50}$ and protein binding affinity is $R^2=0.93$.

Example 6 Lysis of Tumor Cells

αCD3_F F:αBCMA bispecific antibodies were assayed for the ability to kill three different BCMA+ tumor cells and one BCMA-negative cell line through redirection of activated primary T cells. In this experiment, tumor cells were mixed with activated pan T-cells in a 10:1 E:T ratio along with the addition of bispecific antibody. The results are shown in FIGS. 8A-6D. Panel A shows killing of RPMI-8226 cells, panel B shows killing of NCI-H929 cells, panel C shows killing of U-266 cells, and panel D shows killing of K562 cells, a negative control. The x-axis shows the concentration of antibody used and the y-axis shows the % lysis of tumor cells 6 hours after addition of antibody.

The level of IL-2 cytokine release was measured after resting human T cells were cultured with various tumor cell lines and increasing doses of αCD3_F1F:αBCMA bispecific antibody. FIG. 9A shows IL-2 release stimulated by RPMI-8226 cells, FIG. 9B shows IL-2 release stimulated by NCI-H929 cells, FIG. 9C shows IL-2 release stimulated by U-266 cells, and FIG. 9D shows IL-2 release stimulated by K562 cells, a negative control.

The level of IFN-γ cytokine release was measured after resting human T cells were cultured with various tumor cell lines and increasing doses of αCD3_F1F:aBCMA bispecific antibody. FIG. 10A shows IFN-γ release stimulated by RPMI-8226 cells, FIG. 10B shows IFN-γ release stimulated by NCI-H929 cells, FIG. 10C shows IFN-γ release stimulated by U-266 cells, and FIG. 10D shows IFN-γ release stimulated by K562 cells, a negative control.

The examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A bispecific three-chain antibody like molecule comprising:
   (a) a first binding moiety specific for human CD3δ$_ε$, wherein the first binding moiety comprises:
       (i) a first polypeptide subunit comprising a heavy chain variable (VH) domain comprising a CDR1 having an amino acid sequence of GFTFDDYA (SEQ ID NO:29), a CDR2 having an amino acid sequence of ISWNSGSI (SEQ ID NO:24), and a CDR3 having an amino acid sequence of AKDSRGYGDYRLG-GAY (SEQ ID NO:41); and
       (ii) a second polypeptide subunit comprising a light chain variable (VL) domain comprising a CDR1 having an amino acid sequence of QSVSSN (SEQ ID NO:35), a CDR2 having an amino acid sequence of GAS (SEQ ID NO:38), and a CDR3 having an amino acid sequence of QQYNNWPWT (SEQ ID NO:45); and
(b) a second binding moiety specific for human BCMA, wherein the second binding moiety comprises:
(i) a third polypeptide subunit comprising a VH domain comprising a CDR1 having an amino acid sequence of GFTVSSYG (SEQ ID NO:36), a CDR2 having an amino acid sequence of IRGSDGST (SEQ ID NO:39), and a CDR3 having an amino acid sequence of AKQGENDGPFDH (SEQ ID NO:46).

2. The bispecific three-chain antibody like molecule of claim 1, wherein the CDR1, CDR2 and CDR3 sequences in the VH domain of the first polypeptide subunit are present in a human VH framework.

3. The bispecific three-chain antibody like molecule of claim 1, wherein the CDR1, CDR2 and CDR3 sequences in the VL domain of the second polypeptide subunit are present in a human VL framework.

4. The bispecific three-chain antibody like molecule of claim 1, wherein the CDR1, CDR2 and CDR3 sequences in the VH domain of the first polypeptide subunit are present in a human VH framework; and the CDR1, CDR2 and CDR3 sequences in the VL domain of the second polypeptide subunit are present in a human VL framework.

5. The bispecific three-chain antibody like molecule of claim 1, wherein the first polypeptide subunit comprises a VH domain having an amino acid sequence of SEQ ID NO:1.

6. The bispecific three-chain antibody like molecule of claim 5, wherein the third polypeptide subunit comprises a VH domain having an amino acid sequence of SEQ ID NO:21.

7. The bispecific three-chain antibody like molecule of claim 5, wherein the third polypeptide subunit has an amino acid sequence of SEQ ID NO:20.

8. The bispecific three-chain antibody like molecule of claim 1, wherein the second polypeptide subunit comprises a VL domain having an amino acid sequence of SEQ ID NO:19.

9. The bispecific three-chain antibody like molecule of claim 8, wherein the third polypeptide subunit comprises a VH domain having an amino acid sequence of SEQ ID NO:21.

10. The bispecific three-chain antibody like molecule of claim 8, wherein the third polypeptide subunit has an amino acid sequence of SEQ ID NO:20.

11. The bispecific three-chain antibody like molecule of claim 1, wherein the first polypeptide subunit comprises a VH domain having an amino acid sequence of SEQ ID NO:1 and the second polypeptide subunit comprises a VL domain having an amino acid sequence of SEQ ID NO:19.

12. The bispecific three-chain antibody like molecule of claim 1, wherein the third polypeptide subunit comprises a VH domain having an amino acid sequence of SEQ ID NO:21.

13. The bispecific three-chain antibody like molecule of claim 1, wherein the third polypeptide subunit has an amino acid sequence of SEQ ID NO:20.

14. A bispecific three-chain antibody like molecule comprising:
(a) a first binding moiety specific for human $CD3\delta_\epsilon$, wherein the first binding moiety comprises:
(i) a first polypeptide subunit comprising a VH domain having an amino acid sequence of SEQ ID NO:1; and
(ii) a second polypeptide subunit comprising a VL domain having an amino acid sequence of SEQ ID NO:19; and
(b) a second binding moiety specific for human BCMA, wherein the second binding moiety comprises:
(i) a third polypeptide subunit comprising a VH domain having an amino acid sequence of SEQ ID NO:21.

15. The bispecific three-chain antibody like molecule of claim 14, wherein the third polypeptide subunit comprises a first VH domain having an amino acid sequence of SEQ ID NO:21 and a second VH domain having an amino acid sequence of SEQ ID NO:21, wherein the first VH domain and the second VH domain are arranged in a tandem configuration.

16. The bispecific three-chain antibody like molecule of claim 15, wherein the first VH domain and the second VH domain of the third polypeptide subunit are arranged in a tandem configuration and joined by a linker.

17. A bispecific three-chain antibody like molecule comprising:
(a) a first binding moiety specific for human $CD3\delta_\epsilon$, wherein the first binding moiety comprises:
(i) a first polypeptide subunit comprising a VH domain having an amino acid sequence of SEQ ID NO:1; and
(ii) a second polypeptide subunit comprising a VL domain having an amino acid sequence of SEQ ID NO:19; and
(b) a second binding moiety specific for human BCMA, wherein the second binding moiety comprises:
(i) a third polypeptide subunit having an amino acid sequence of SEQ ID NO:20.

\* \* \* \* \*

UNITED STATES PATENT AND TRADEMARK OFFICE
CERTIFICATE OF CORRECTION

PATENT NO. : 11,421,027 B2
APPLICATION NO. : 17/492444
DATED : August 23, 2022
INVENTOR(S) : Nathan Trinklein et al.

It is certified that error appears in the above-identified patent and that said Letters Patent is hereby corrected as shown below:

In the Claims

Column 57 In Claim 1, Line 63, the phrase "CD3$\delta_\varepsilon$." should be changed to -- CD3$\delta\varepsilon$ --.

Column 60 In Claim 14, Line 12, the phrase "CD3$\delta_\varepsilon$." should be changed to -- CD3$\delta\varepsilon$ --.

Column 60 In Claim 17, Line 37, the phrase "CD3$\delta_\varepsilon$." should be changed to -- CD3$\delta\varepsilon$ --.

Signed and Sealed this
Second Day of May, 2023

Katherine Kelly Vidal
*Director of the United States Patent and Trademark Office*